(12) United States Patent
Ma et al.

(10) Patent No.: US 11,903,976 B2
(45) Date of Patent: *Feb. 20, 2024

(54) IMPLANTABLE THERAPEUTIC DELIVERY SYSTEM HAVING A NANOFIBROUS CORE

(71) Applicant: CORNELL UNIVERSITY, Ithaca, NY (US)

(72) Inventors: Minglin Ma, Ithaca, NY (US); James A. Flanders, Ithaca, NY (US); Duo An, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/666,987

(22) Filed: Oct. 29, 2019

(65) Prior Publication Data

US 2020/0171095 A1    Jun. 4, 2020

Related U.S. Application Data

(63) Continuation of application No. 15/317,657, filed as application No. PCT/US2015/034853 on Jun. 9, 2015, now Pat. No. 10,493,107.

(Continued)

(51) Int. Cl.
*A61K 35/39* (2015.01)
*A61K 9/00* (2006.01)
(Continued)

(52) U.S. Cl.
CPC ............ *A61K 35/39* (2013.01); *A61K 9/0024* (2013.01); *A61K 9/06* (2013.01); *A61K 9/146* (2013.01);
(Continued)

(58) Field of Classification Search
CPC ........ A61K 35/39; A61K 9/0024; A61K 9/06; A61K 9/146; A61K 35/28; A61K 47/36; A61K 2035/128
See application file for complete search history.

(56) References Cited

U.S. PATENT DOCUMENTS 5,885,980 A * 3/1999 Gutierrez ............... A61K 31/64
514/186
6,372,244 B1 4/2002 Antanavich et al.
(Continued)

FOREIGN PATENT DOCUMENTS

| | | |
|---|---|---|
| CN | 101227913 A | 7/2008 |
| CN | 101426530 A | 5/2009 |

(Continued)

OTHER PUBLICATIONS

An, Duo et al. "Developing robust, hydrogel-based, nano-fiber-enabled encapsulation devices (NEEDS) for cell therapies", Biomaterials 37 (Oct. 2014), pp. 40-48. (Year: 2014).*

(Continued)

*Primary Examiner* — Carlos A Azpuru
*Assistant Examiner* — Casey S Hagopian
(74) *Attorney, Agent, or Firm* — Troutman Pepper Hamilton Sanders LLP (Rochester)

(57) ABSTRACT

Disclosed are an implantable therapeutic delivery system and methods of treatment utilizing the implantable therapeutic delivery system. The implantable therapeutic delivery system includes a nanofibrous core substrate including one or more internal spaces wherein one or more therapeutic agents is positioned in the one or more internal spaces; and an outer biocompatible polymeric coating surrounding said nanofibrous core substrate.

13 Claims, 29 Drawing Sheets

Related U.S. Application Data

(60) Provisional application No. 62/009,674, filed on Jun. 9, 2014.

(51) Int. Cl.
    *A61K 47/36*     (2006.01)
    *A61K 35/28*     (2015.01)
    *A61K 35/12*     (2015.01)
    *A61K 9/06*      (2006.01)
    *A61K 9/14*      (2006.01)

(52) U.S. Cl.
    CPC ............. *A61K 35/28* (2013.01); *A61K 47/36* (2013.01); *A61K 2035/128* (2013.01)

(56) References Cited

U.S. PATENT DOCUMENTS

| | | | |
|---|---|---|---|
| 8,071,722 B2 | 12/2011 | Kaplan et al. | |
| 8,278,106 B2 | 10/2012 | Martinson et al. | |
| 8,425,928 B2 | 4/2013 | Martinson et al. | |
| 2003/0232198 A1* | 12/2003 | Lamberti | A61L 27/24 428/480 |
| 2004/0033947 A1* | 2/2004 | Ohrstrom | A61K 38/4846 424/94.5 |
| 2006/0024350 A1* | 2/2006 | Varner | A61F 9/0017 424/427 |
| 2006/0121080 A1* | 6/2006 | Lye | A61L 31/18 623/1.42 |
| 2006/0193769 A1* | 8/2006 | Nelson | A61P 43/00 424/1.11 |
| 2007/0077270 A1* | 4/2007 | Wen | A61F 11/00 424/423 |
| 2009/0182303 A1 | 7/2009 | Walak et al. | |
| 2018/0140619 A1* | 5/2018 | Sinha | A61K 31/655 |

FOREIGN PATENT DOCUMENTS

| | | | |
|---|---|---|---|
| CN | 101563116 A | 12/2009 | |
| CN | 101778891 A | 7/2010 | |
| CN | 101897995 A | 12/2010 | |
| CN | 102196826 A | 9/2011 | |
| CN | 202605378 U | 12/2012 | |
| CN | 103705325 A | 4/2014 | |
| EP | 2389896 A2 | 11/2011 | |
| WO | 91/09119 A1 | 6/1991 | |
| WO | 2001/02452 A1 | 1/2001 | |
| WO | 2005/102406 A1 | 11/2005 | |
| WO | 2008/079997 A2 | 7/2008 | |
| WO | 2013134360 A1 | 9/2013 | |

OTHER PUBLICATIONS

Onoe et al., "Metre-Long Cell-Laden Microfibres Exhibit Tissue Morphologies and Functions," Nature Materials 12(6):584-590 (2013).

Rowley et al., "Hydrogels Used for Cell-Based Drug Delivery," Journal of Biomedical Materials Research, Part A 87(4):1113-1122 (2008).

Lee et al., "Cell Transplantation for Endocrine Disorders," Advanced Drug Delivery Reviews 42(1-2):103-120 (2000).

Lee et al., "Synthesis of Cell-Laden Alginate Hollow Fibers Using Microfluidic Chips and Microvascularized Tissue-Engineering Applications," Small 5(11):1264-1268 (2009).

Akbari et al., "Composite Living Fibers for Creating Tissue Constructs Using Textile Techniques," Advanced Functional Materials 24(26):4060-4067 (2014).

English Translation and First Office Action for China Application No. 201580039185.X (dated Jul. 24, 2019).

European Search Report in corresponding EP15806324.8 dated Apr. 5, 2018.

An et al., "Developing Robust, Hydrogel-based, Nanofiber-enabled Encapsulation Devices (NEEDs) for Cell Therapies," Biomaterials 37:40-48 (2015).

Bruin et al., "Treating Diet-induced Diabetes and Obesity with Human Embryonic Stem Cell-derived Pancreatic Progenitor Cells and Antidiabetic Drugs," Stem Cell Reports 4:605-620 (2015).

Kumagai-Braesch et al., "The TheraCyte Device Protects Against Islet Allograft Rejection in Immunized Hosts," Cell Transplantation 22:1137-1146 (2013).

PCT International Search Report and Written Opinion corresponding to PCT/US2015/034853, filed Jun. 9, 2015 (dated Aug. 25, 2015).

English Translation and Second Office Action for China Application No. 201580039185.X (dated Jun. 12, 2020).

* cited by examiner

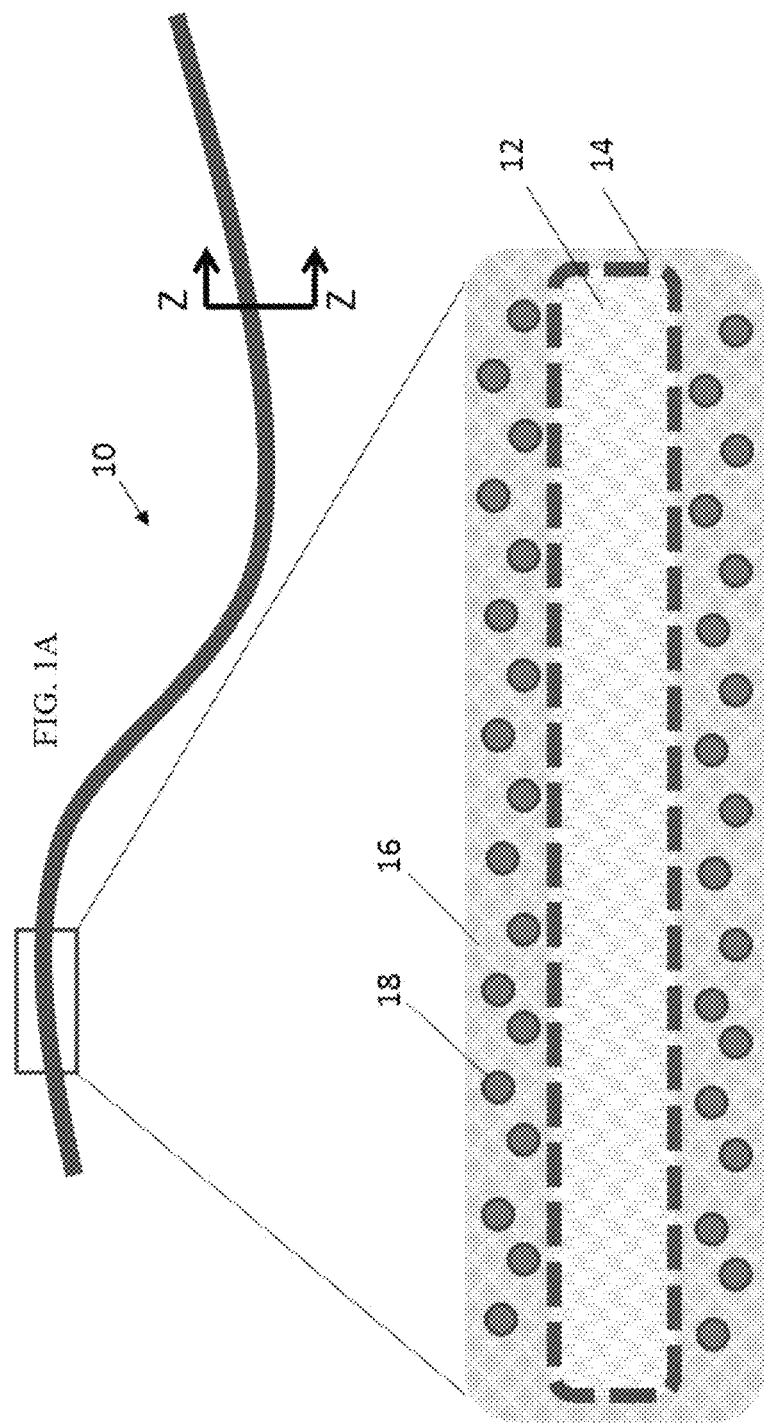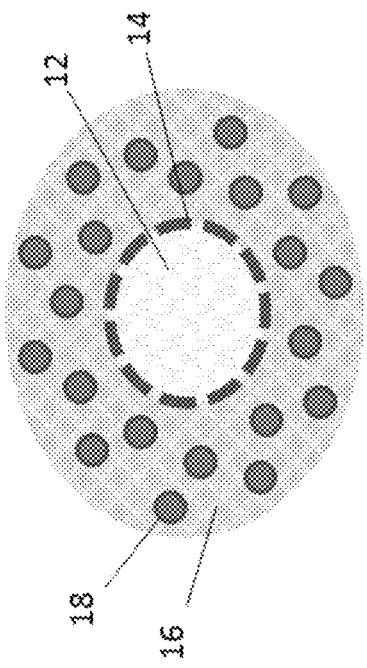

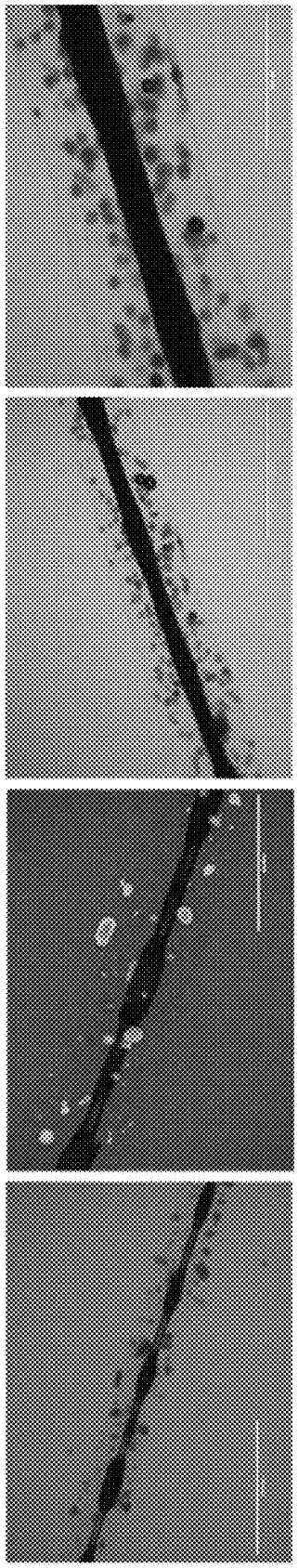
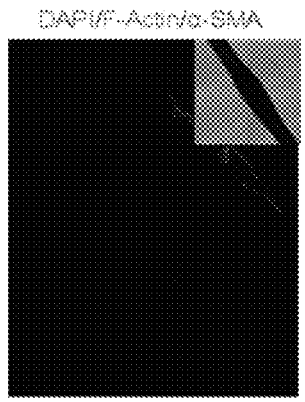 
FIG. 2N  FIG. 3D  FIG. 3H
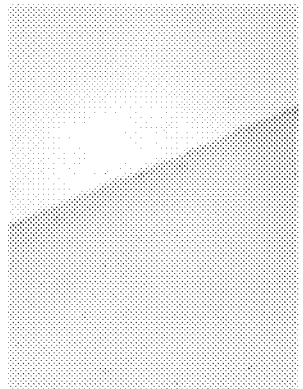 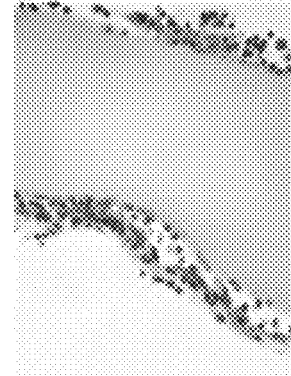
FIG. 2M  FIG. 3C  FIG. 3G
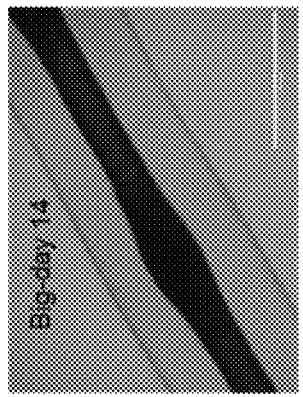 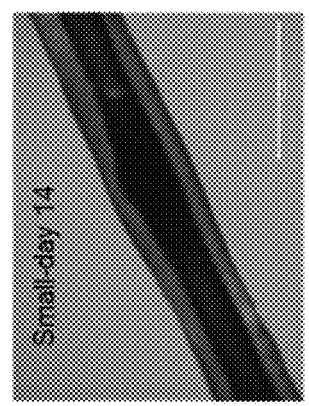
FIG. 2L  FIG. 3B  FIG. 3F
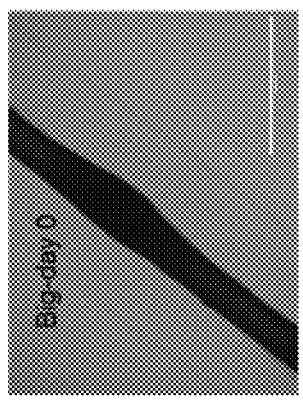 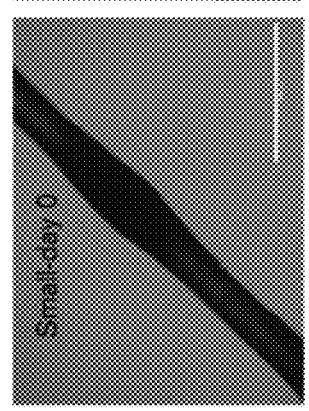
FIG. 2K  FIG. 3A  FIG. 3E

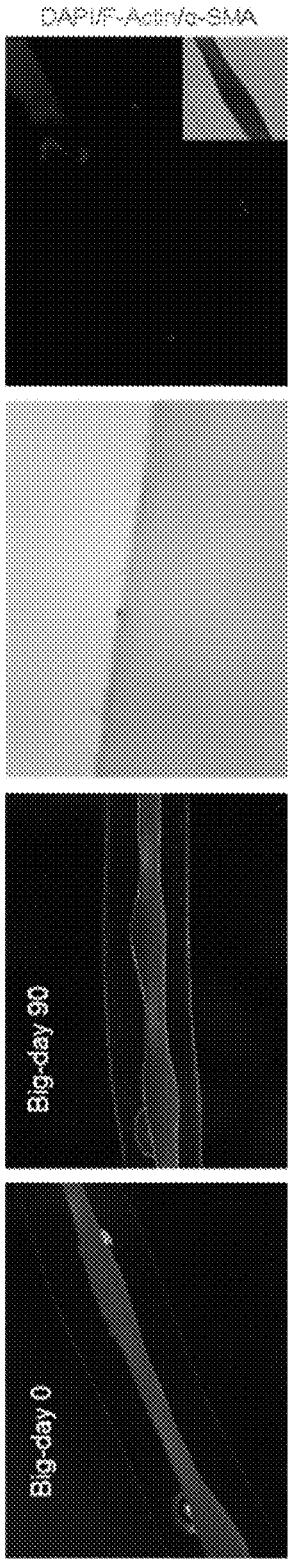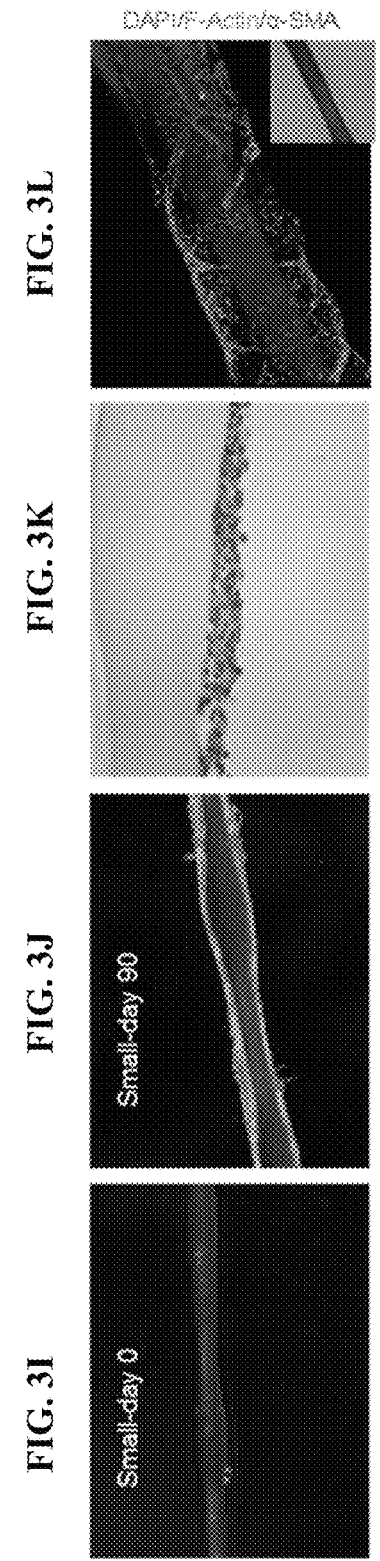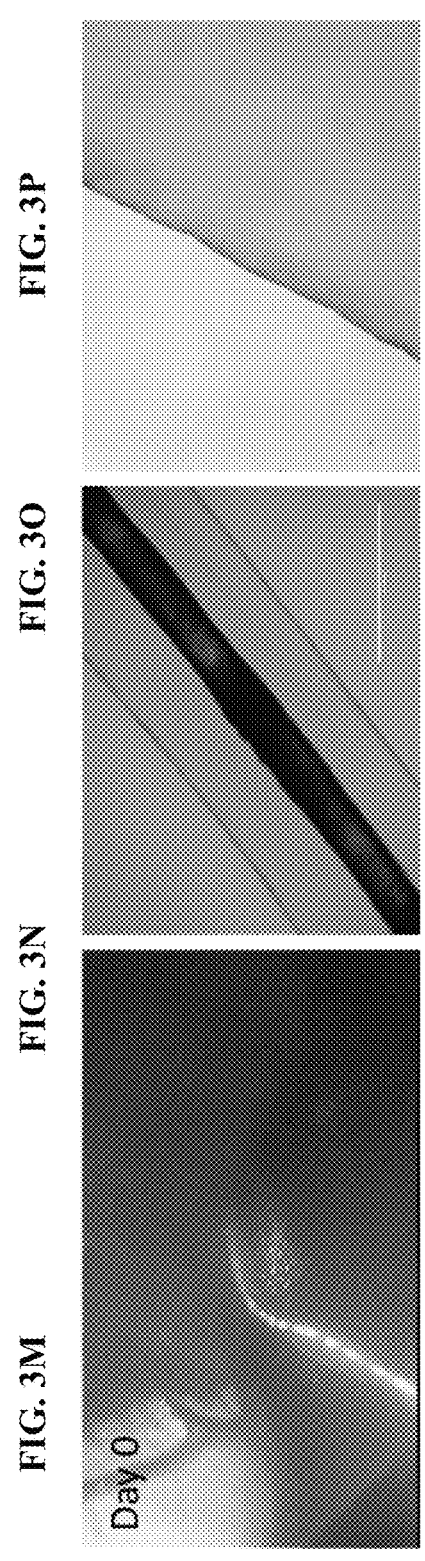

FIG. 4D
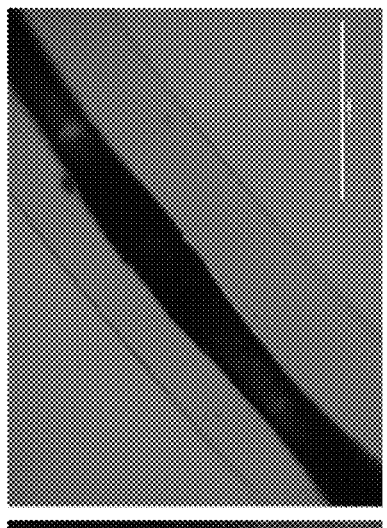
FIG. 4E
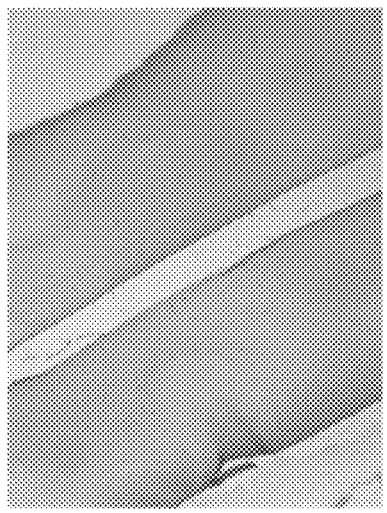
FIG. 4F
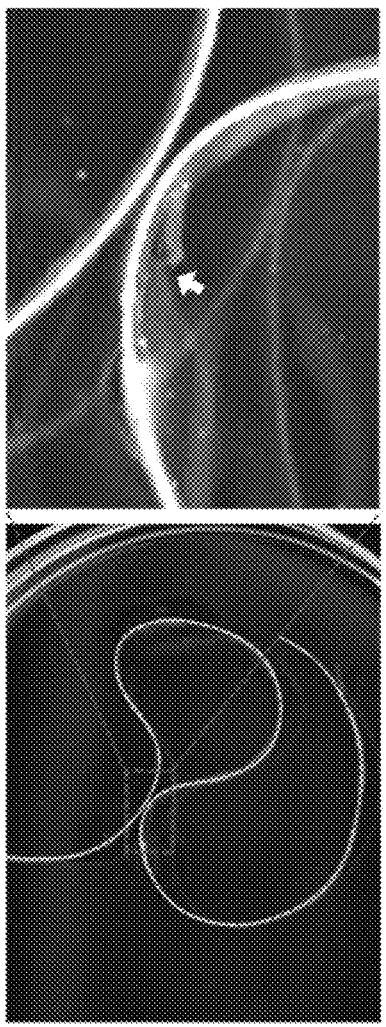
FIG. 4I
FIG. 4H
FIG. 4G

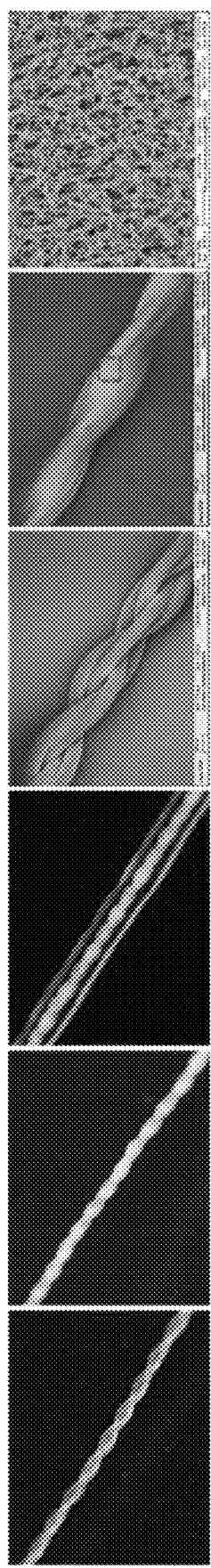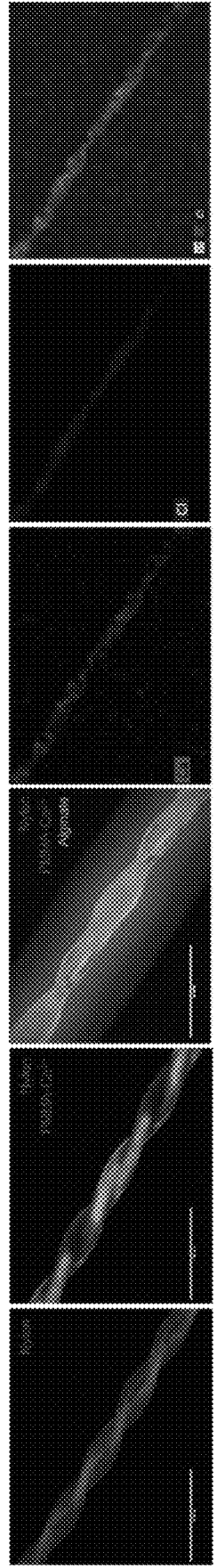

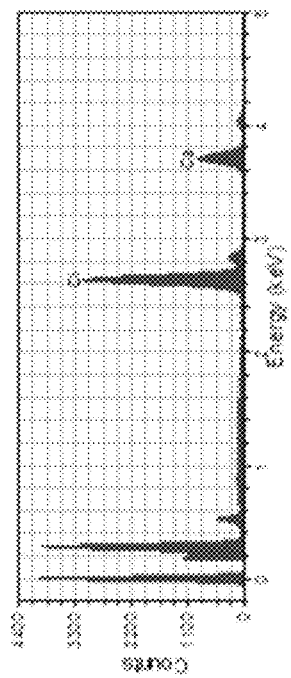
FIG. 5O
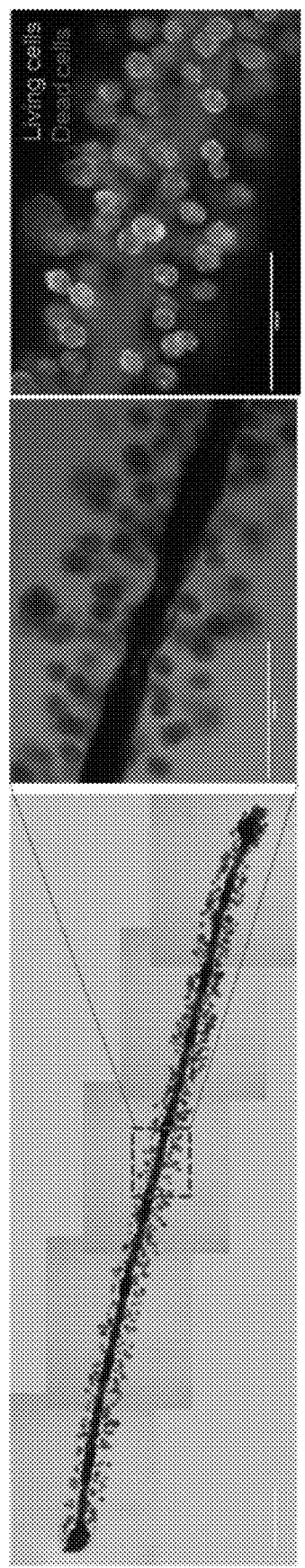
FIG. 5P
FIG. 5Q
FIG. 5R

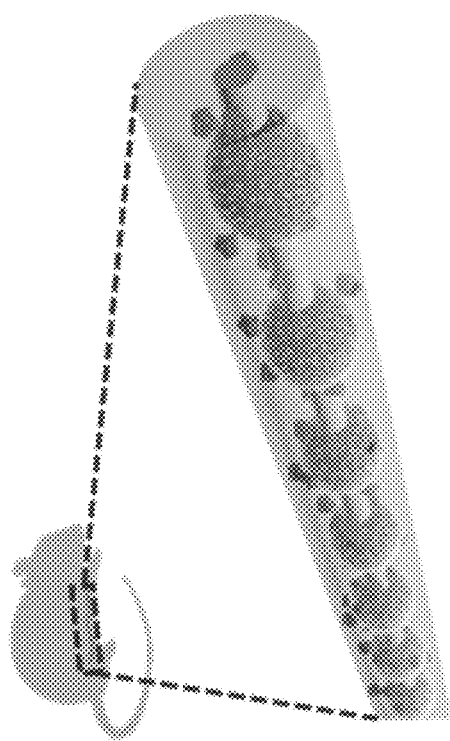
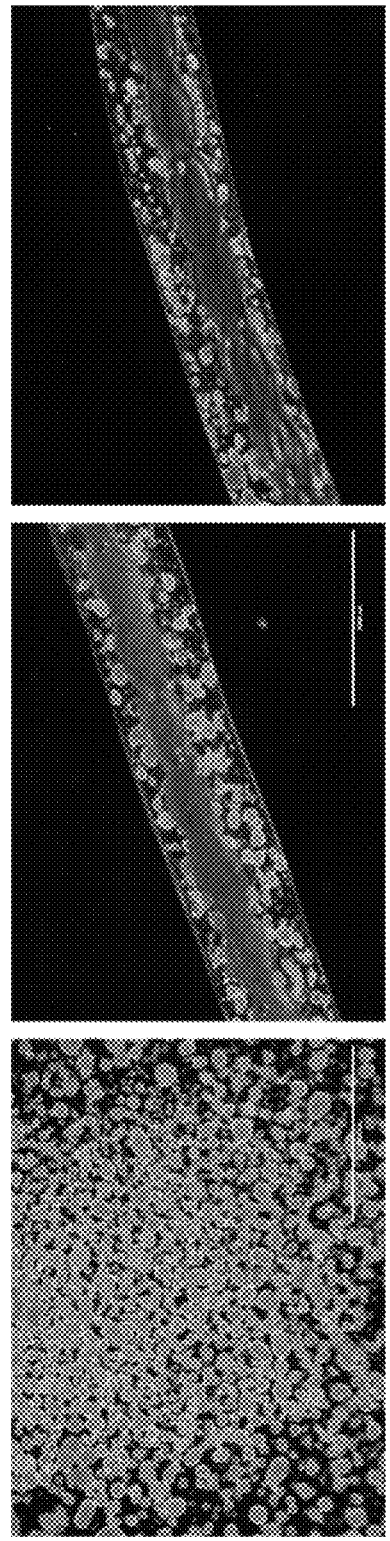
FIG. 6A
FIG. 6B
FIG. 6C
FIG. 6D

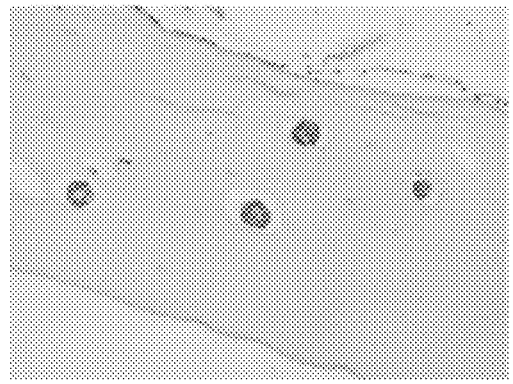 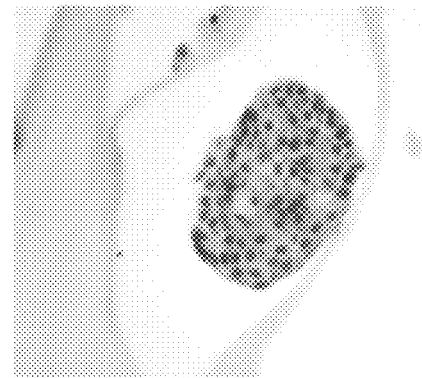
FIG. 6E  FIG. 6F
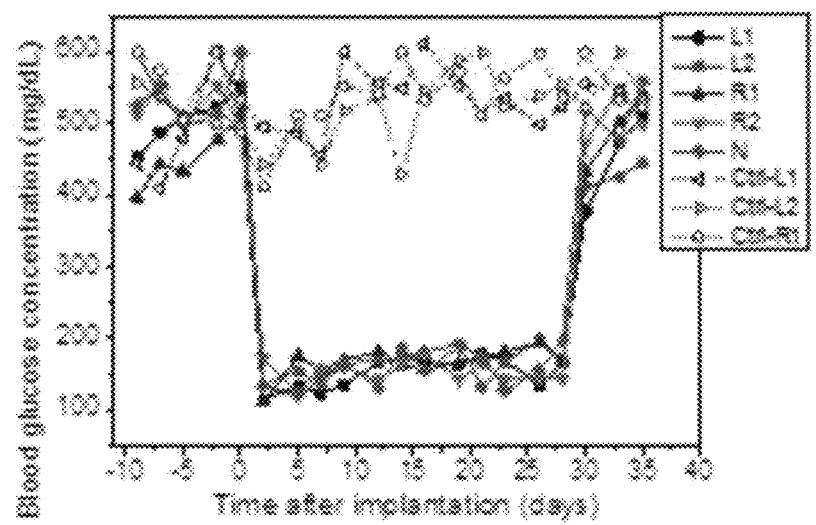
FIG. 6G

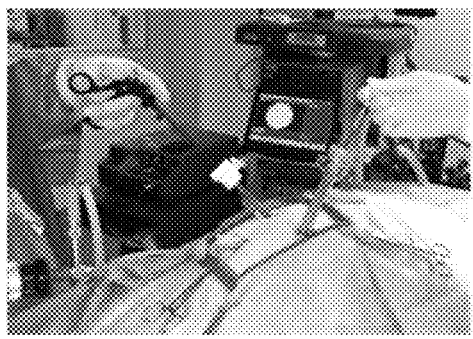 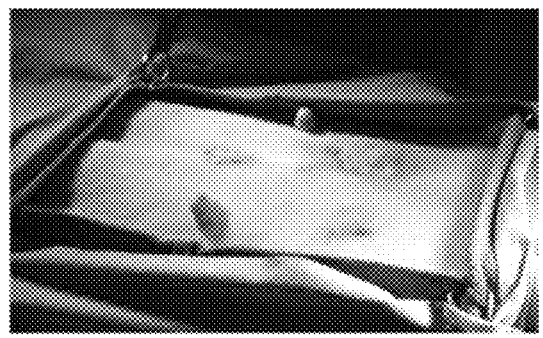
FIG. 7B　　　　　　　FIG. 7C
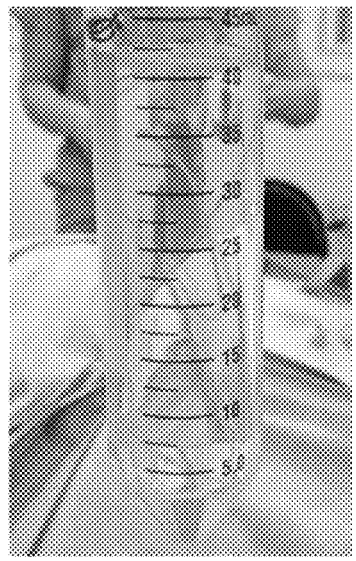
FIG. 7D
 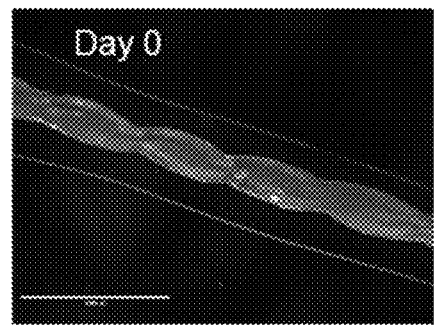
FIG. 7E　　　　　　　FIG. 7F

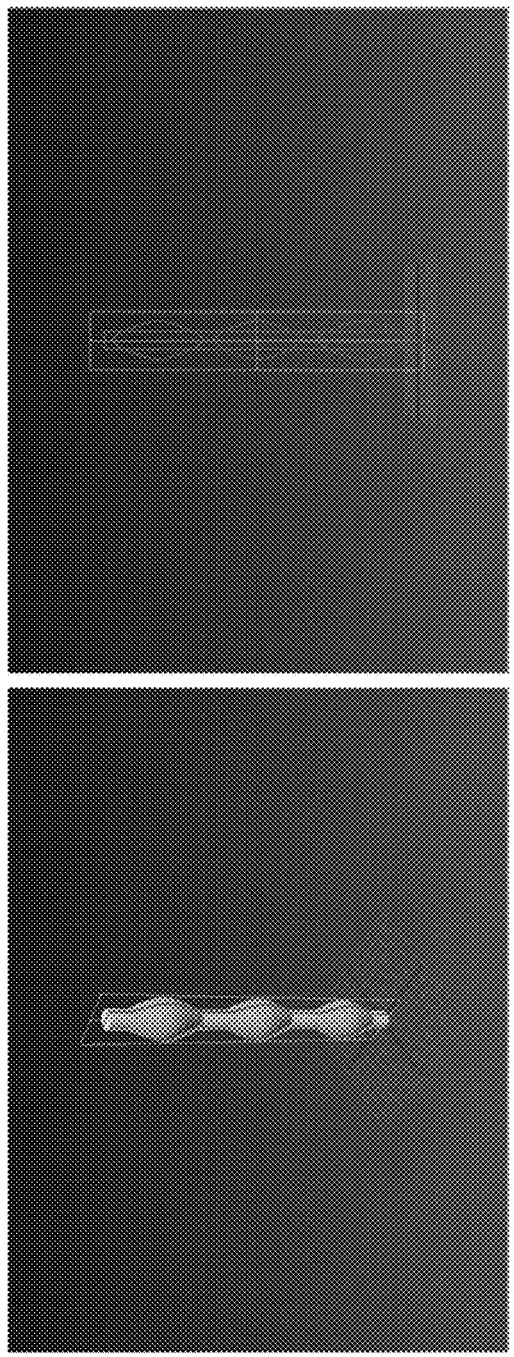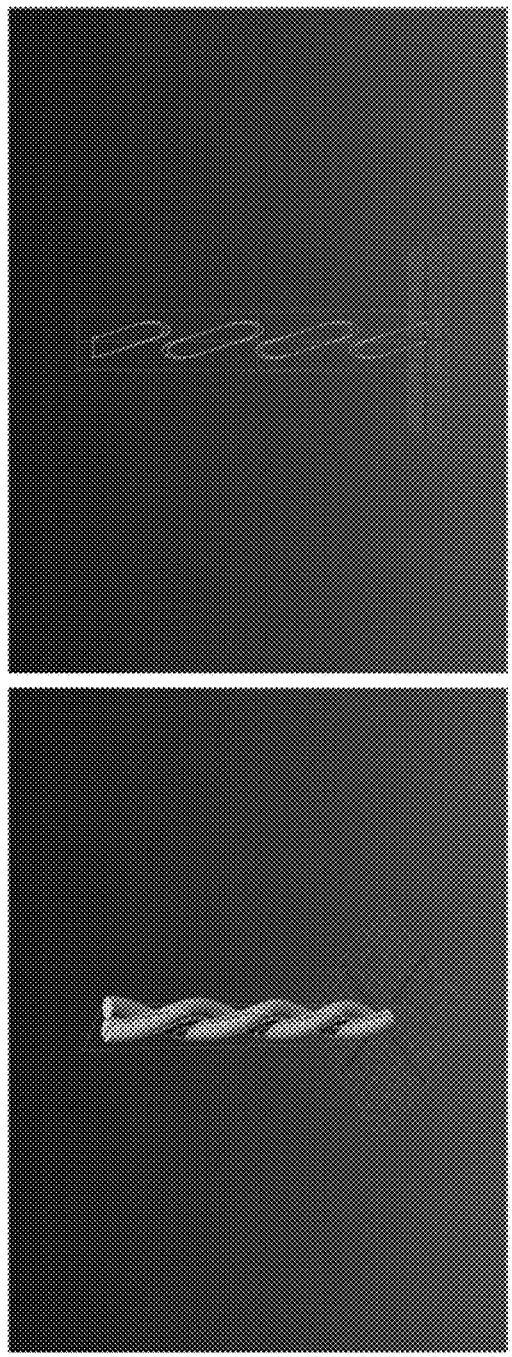
FIG. 12A  FIG. 12B  FIG. 12C  FIG. 12D

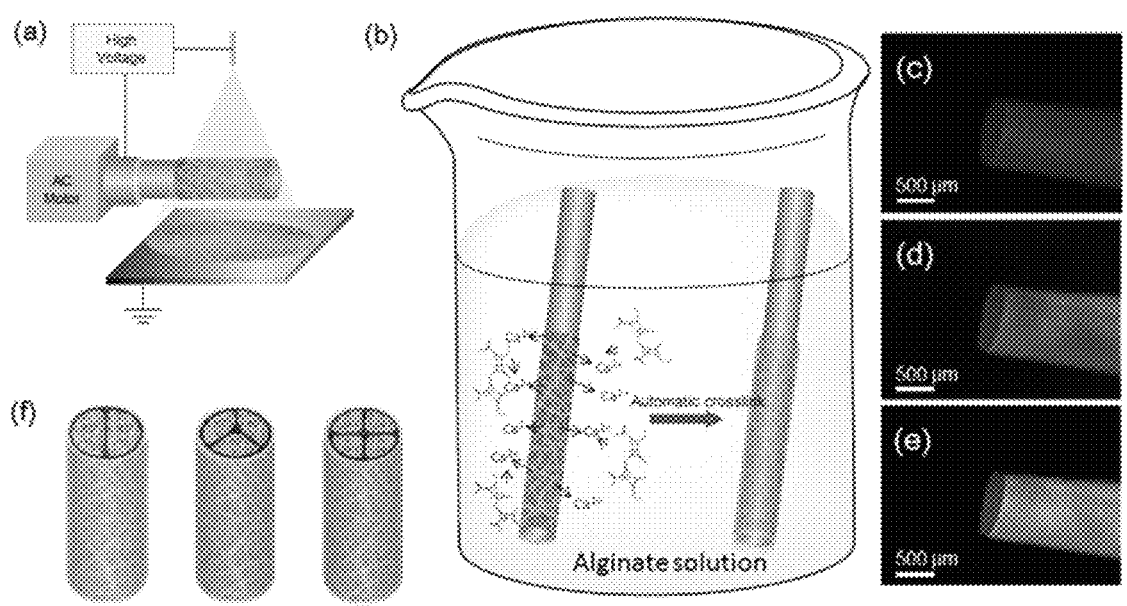
FIGs. 16A-F

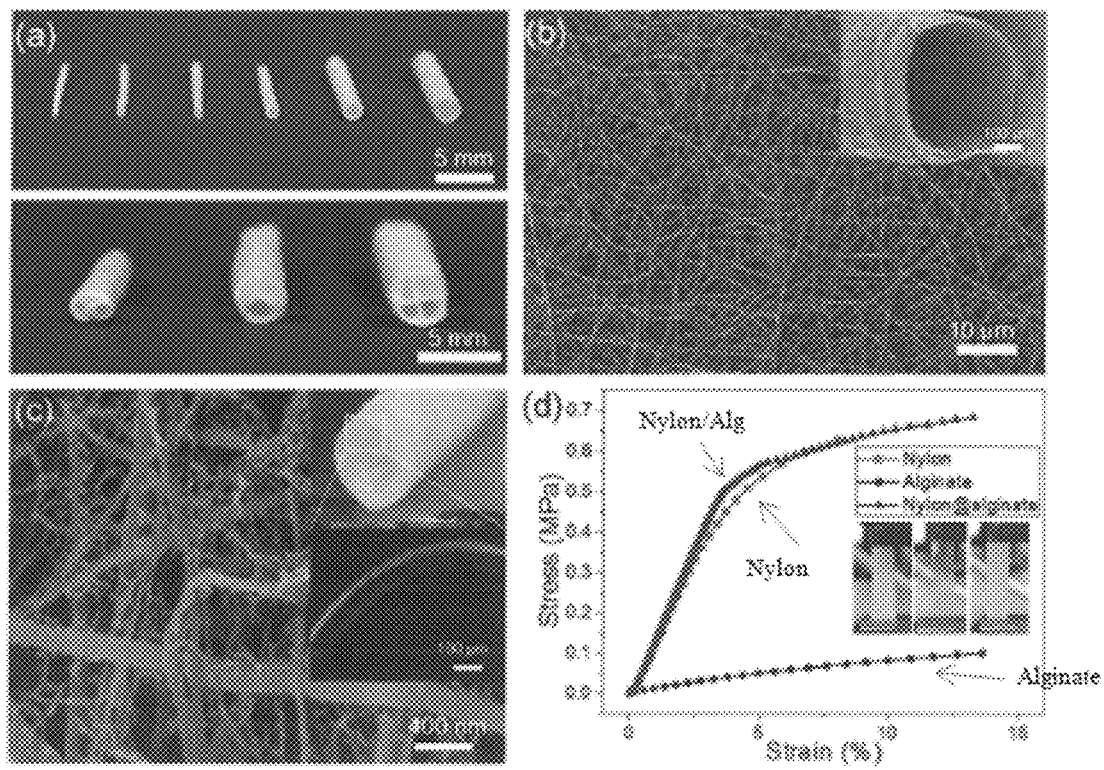
FIGs. 17A-D

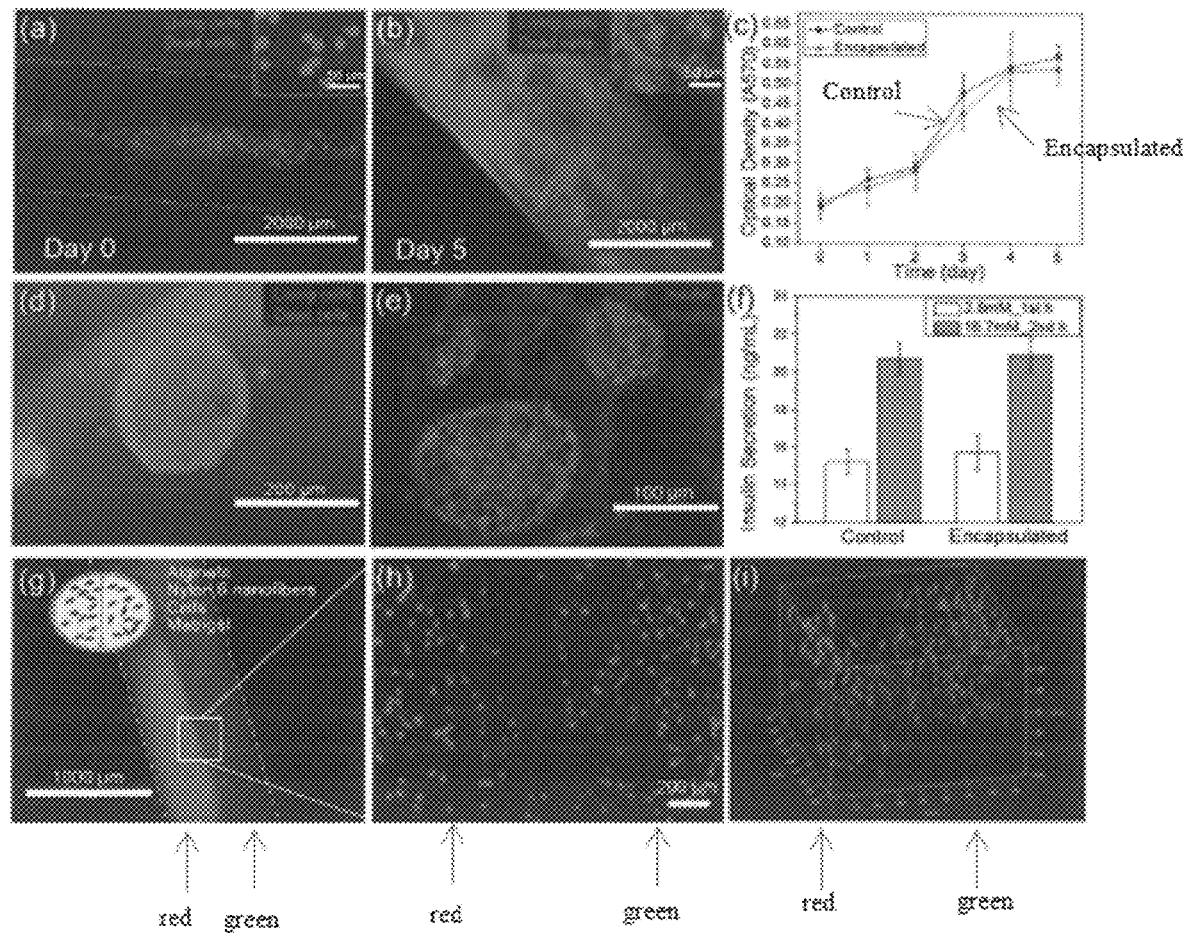
FIGs. 18A-I

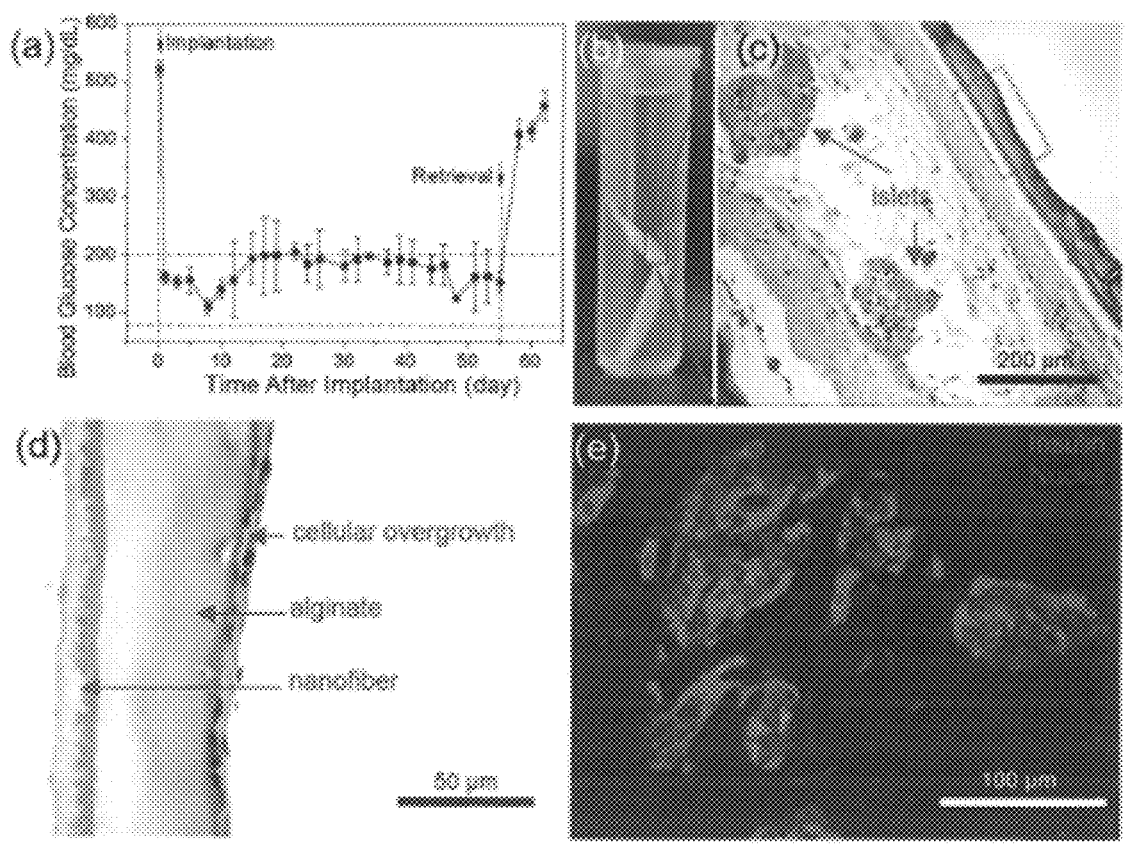
FIGs. 19A-E

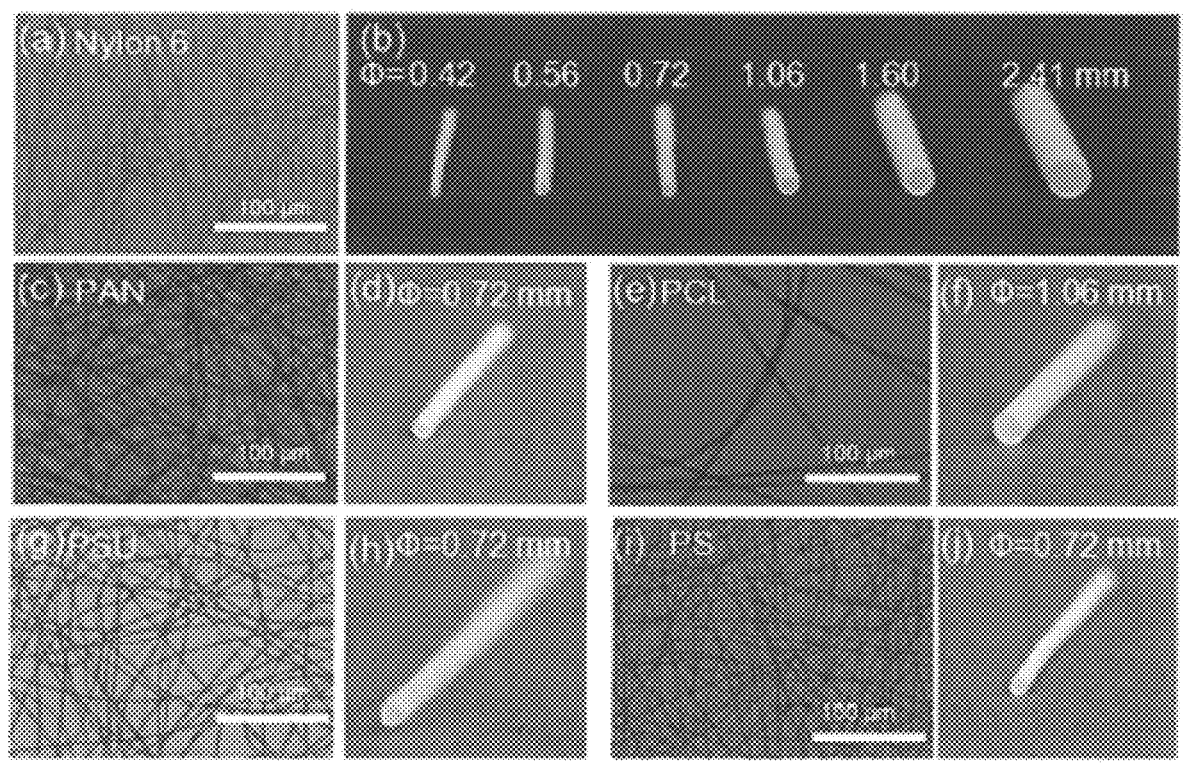
FIGs. 20A-J

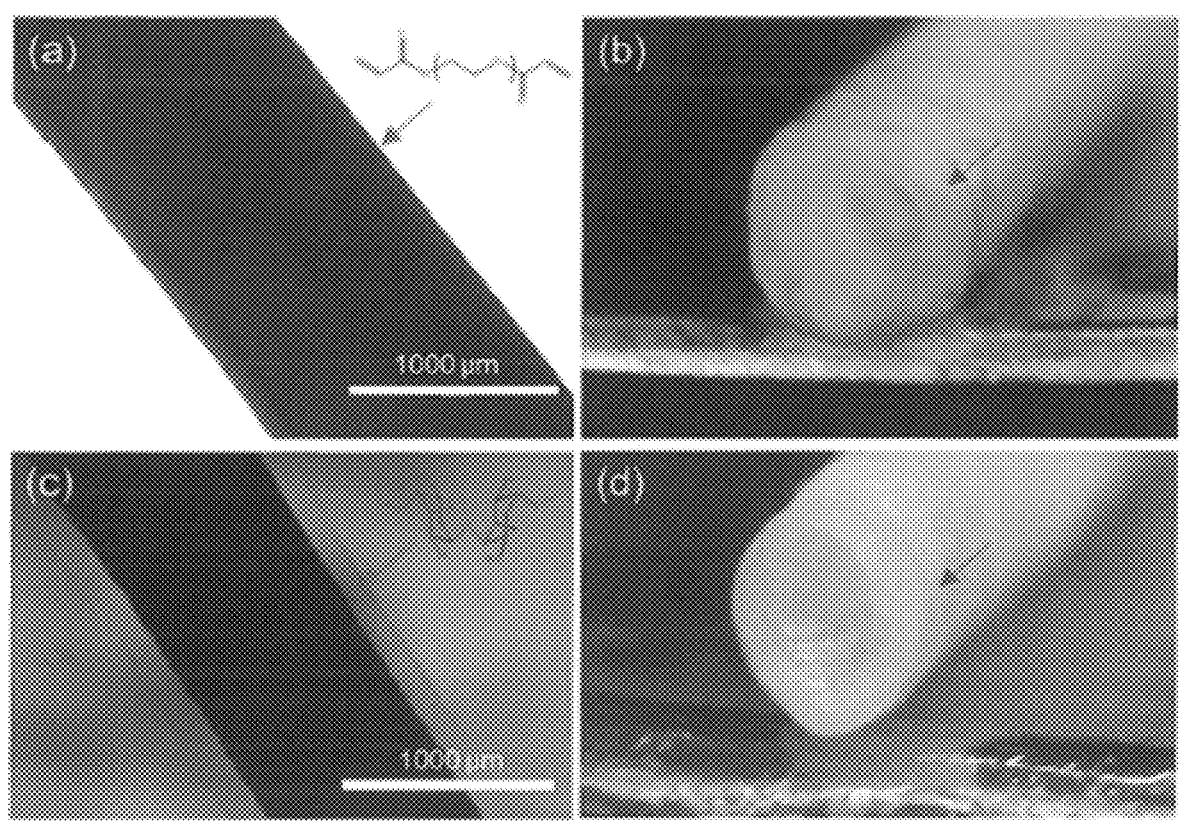
FIGs. 21A-D

IMPLANTABLE THERAPEUTIC DELIVERY SYSTEM HAVING A NANOFIBROUS CORE

This application is a continuation of U.S. patent application Ser. No. 15/317,657, filed Dec. 9, 2016, which is a 371 of International Patent Application Serial No. PCT/US2015/034853, filed Jun. 9, 2015, all which claim the benefit of U.S. Provisional Patent Application Ser. No. 62/009,674, filed Jun. 9, 2014, each of which are hereby incorporated by reference in its entirety.

FIELD OF THE INVENTION

The present invention relates to an implantable therapeutic delivery system, methods of treatment utilizing the implantable therapeutic delivery system, and methods of fabricating the implantable delivery system.

BACKGROUND OF THE INVENTION

Type 1 Diabetes ("T1D") is an autoimmune disease in which the body's own immune system attacks and destroys the insulin-producing beta cells in the pancreas. It is estimated that T1D affects as many as 3 million people in the U.S. alone, with 80 new patients diagnosed every day. The rate of T1D incidence among children under the age of 14 is estimated to increase by 3% annually worldwide. Although careful and tight control of blood glucose level by injections or infusion of exogenous insulin allows a T1D patient to stay alive, the approach requires constant attention and strict compliance. It does not cure the disease or prevent its many devastating effects such as blindness, hypertension, kidney disease, neuropathy, vascular disease, heart disease, and stroke (The Diabetes Control and Complications Trial Research Group, "The Effect of Intensive Treatment of Diabetes on the Development and Progression of Long-Term Complications in Insulin-Dependent Diabetes Mellitus," *N. Engl. J. Med.* 329:977-986 (1993) and Writing Team for the Diabetes Complications Trial/Epidemiology of Diabetes & Complications Research, "Sustained Effect of Intensive Treatment of Type 1 Diabetes Mellitus on Development and Progression of Diabetic Nephropathy: The Epidemiology of Diabetes Interventions and Complications (EDIC) Study," *JAMA* 290:2159-2167 (2003)).

Transplantation of islet cells provides a potential alternative treat treatment for T1D and has been shown to restore normoglycemia (Shapiro et al., "Islet Transplantation in Seven Patients with Type 1 Diabetes Mellitus Using a Glucocorticoid-Free Immunosuppressive Regimen," *N. Engl. J. Med.* 343:230-238 (2000) and Shapiro et al., "International Trial of the Edmonton Protocol for Islet Transplantation," *N. Engl. J. Med.* 355:1318-1330 (2006)). However, to avoid immune rejections, the patients need to take long-term immunosuppressive drugs that are known to cause deleterious side effects (Weir et al., "Scientific and Political Impediments to Successful Islet Transplantation," *Diabetes* 46:1247-1256 (1997) and Naftanel et al., "Pancreatic Islet Transplantation," *PLoS Med.* 1:e58 (2004)). The wide application of islet cell transplantation is also limited by a great shortage of appropriate donors (Weir et al., "Scientific and Political Impediments to Successful Islet Transplantation," *Diabetes* 46:1247-1256 (1997) and Naftanel et al., "Pancreatic Islet Transplantation," *PLoS Med.* 1:e58 (2004)).

Transplantation of encapsulated, immuno-protected islet cells is a much more attractive and extremely promising way to reverse T1D (Chang, "Therapeutic Applications of Polymeric Artificial Cells," *Nat. Rev. Drug Discov.* 4:21-235 (2005); Orive et al., "Cell Encapsulation: Promise and Progress," *Nat. Med.* 9:104-107 (2003); and Calafiore, "Alginate Microcapsules for Pancreatic Islet Cell Graft Immunoprotection: Struggle and Progress Towards the Final Cure for Type 1 Diabetes Mellitus," *Expert Opin. Biol. Ther.* 3:201-205 (2003)). Islet cell transplantation avoids life-long immunosuppression, and also allows the use of other types of cells such as xenogeneic islets from pigs (Brandhorst et al., "Isolation of Islands of Langerhans from Human and Porcine Pancreas for Transplantation to Humans," *Zentralbl. Chir.* 123:814-822 (1998); O'Sullivan et al., "Islets Transplanted in Immunoisolation Devices: A Review of the Progress and the Challenges that Remain," *Endocr. Rev.* 32:827-844 (2011); and Dufrane et al., "Macro- or Microencapsulation of Pig Islets to Cure Type 1 Diabetes," *World J. Gastroenterol.* 18:6885-6893 (2012)) or stem cell-derived ones (Kroon et al., "Pancreatic Endoderm Derived from Human Embryonic Stem Cells Generates Glucose-Responsive Insulin-Secreting Cells In vivo," *Nat. Biotechnol.* 26:443-452 (2008) and Rezania et al., "Maturation of Human Embryonic Stem Cell-Derived Pancreatic Progenitors Into Functional Islets Capable of Treating Pre-Existing Diabetes in Mice," *Diabetes* 61:2016-2029 (2012)). The encapsulating material or device protects the islets from the host immune rejection while simultaneously allowing facile mass transfer to maintain their survival and function.

Despite the huge research efforts worldwide and the significant progress that has been made in the last three decades, clinical application of encapsulation of islets cells has remained elusive due to a lack of translatable encapsulation systems (Scharp et al., "Encapsulated Islets for Diabetes Therapy: History, Current Progress, and Critical Issues Requiring Solution," *Adv. Drug Deliv. Rev.* 67-68:35-73 (2013)). Currently, there are two major types of islet cell encapsulation systems: macroscopic devices and hydrogel microcapsules, both of which unfortunately have serious limitations. The macroscopic encapsulation devices, such as diffusion chambers (Geller et al., "Use of an Immunoisolation Device for Cell Transplantation and Tumor Immunotherapy," *Ann. N.Y. Acad. Sci.* 831:438-451 (1997)), hydrogel sheet (Dufrane et al., "Alginate Macroencapsulation of Pig Islets Allows Correction of Streptozotocin-Induced Diabetes in Primates Up to 6 Months Without Immunosuppression," *Transplantation* 90:1054-1062 (2010)) or porous polymer hollow tubes (Lacy et al., "Maintenance of Normoglycemia in Diabetic Mice by Subcutaneous Xenografts of Encapsulated Islets," *Science* 254:1782-1784 (1991)) are often bulky or fragile, and suffer from insufficient biocompatibility and inadequate mass transfer (Colton, "Implantable Biohybrid Artificial Organs," *Cell Transplant.* 4:415-436 (1995); Kühtreiber et al., *Cell Encapsulation Technology and Therapeutics*, Birkhauser, Boston, 1999; Vaithilingam et al., "Islet Transplantation and Encapsulation: An Update on Recent Developments," *Rev. Diabet. Stud.* 8:51-67 (2011); and Soon-Shiong, "Treatment of Type I Diabetes Using Encapsulated Islets," *Adv. Drug Deliv. Rev.* 35:259-270 (1999)).

Alginate hydrogel microcapsules, on the other hand, are easy to transplant, have larger surface area for mass transfer, and significant progress has been made recently on their biocompatibility and long term function (Calafiore, "Alginate Microcapsules for Pancreatic Islet Cell Graft Immunoprotection: Struggle and Progress Towards the Final Cure for Type 1 Diabetes Mellitus," *Expert Opin. Biol. Ther.* 3:201-205 (2003); Vaithilingam et al., "Islet Transplantation and Encapsulation: An Update on Recent Developments," *Rev. Diabet. Stud.* 8:51-67 (2011); Smink et al., "Toward Engineering a Novel Transplantation Site for Human Pancreatic Islets," *Diabetes* 62:1357-1364 (2013); Jacobs-Tulleneers-Thevissen et al., "Sustained Function of Alginate-Encapsulated Human Islet Cell Implants in the Peritoneal Cavity of Mice Leading to a Pilot Study in a Type 1 Diabetic Patient," *Diabetologia* 56:1605-1614 (2013); and Dolgin, "Encapsulate This," Nat. *Med.* 20:9-11 (2014)). However, a major challenge is that after the capsules are transplanted, often in high number (~100,000) within the peritoneal cavity, it is almost impossible to reliably and completely retrieve or replace them in the event of medical complications or transplant failure (Calafiore, "Alginate Microcapsules for Pancreatic Islet Cell Graft Immunoprotection: Struggle and Progress Towards the Final Cure for Type 1 Diabetes Mellitus," *Expert Opin. Biol. Ther.* 3:201-205 (2003); Vaithilingam et al., "Islet Transplantation and Encapsulation: An Update on Recent Developments," *Rev. Diabet. Stud.* 8:51-67 (2011); Smink et al., "Toward Engineering a Novel Transplantation Site for Human Pancreatic Islets," *Diabetes* 62:1357-1364 (2013); and Jacobs-Tulleneers-Thevissen et al., "Sustained Function of Alginate-Encapsulated Human Islet Cell Implants in the Peritoneal Cavity of Mice Leading to a Pilot Study in a Type 1 Diabetic Patient," *Diabetologia* 56:1605-1614 (2013)). This raises patients' concerns over the permanent implantation of biomaterials and foreign cells within their body. There is also a risk of potential teratoma formation when stem cells are used. Additionally, the inability to retrieve the entire implant makes it impossible for physicians and researchers to examine the transplant in its entirety after failure.

Hydrogel microfibers, such as those made from alginate, have received much attention recently as a potentially biocompatible, high surface area platform to encapsulate cells for various applications (Onoe et al., "Metre-Long Cell-Laden Microfibres Exhibit Tissue Morphologies and Functions," *Nat. Mater.* 12:584-590 (2013); Raof et al., "One-Dimensional Self-Assembly of Mouse Embryonic Stem Cells Using an Array of Hydrogel Microstrands," *Biomaterials* 32:4498-4505 (2011); Lee et al., "Synthesis of Cell-Laden Alginate Hollow Fibers Using Microfluidic Chips and Microvascularized Tissue-Engineering Applications," *Small* 5:1264-1268 (2009); Zhang et al., "Creating Polymer Hydrogel Microfibres with Internal Alignment Via Electrical and Mechanical Stretching," *Biomaterials* 35(10):3243-3251 (2014); Yu et al., "Flexible Fabrication of Biomimetic Bamboo-Like Hybrid Microfibers," *Adv. Mater.* 26(16): 2494-2499 (2014)). These microfibers are generally produced by microfluidic approaches. They are scalable from millimeters to meters long and can be further woven using thin capillaries and fluidic flows (Onoe et al., "Metre-Long Cell-Laden Microfibres Exhibit Tissue Morphologies and Functions," *Nat. Mater.* 12:584-590 (2013)). However, the intrinsic mechanical weakness of hydrogel materials, especially those suitable for cell encapsulation applications, and a high aspect ratio make hydrogel microfibers easy to break and difficult to handle. Both issues are significant concerns for eventual clinical applications.

Host recognition and subsequent foreign body responses can cause the failure of transplanted biomedical devices. Even though alginate hydrogel has been considered a relatively biocompatible material and has been used in many clinical trials, it still can cause foreign body reactions that lead to fibrotic cellular overgrowth and collagen deposition. It is known that the geometry of the transplanted materials can significantly influence fibrosis.

The present invention overcomes past deficiencies in the creation of hydrogel implants for treatment of diabetes, e.g., type 1 diabetes or type 2 diabetes.

SUMMARY OF THE INVENTION

A first aspect of the present invention is directed to an implantable therapeutic delivery system. This therapeutic delivery system comprises a substrate, an inner polymeric coating that surrounds the substrate, and an outer hydrogel coating that surrounds said inner polymeric coating. One or more therapeutic agents are positioned in the outer hydrogel coating.

Another aspect of the present invention is directed to a method of delivering a therapeutic agent to a subject. This method involves providing a subject in need of a therapeutic agent and implanting the implantable therapeutic delivery system described herein into the subject.

A further aspect of the present invention is directed to a method of treating a subject. This method involves implanting the implantable therapeutic delivery system described herein into a subject with diabetes.

Another aspect of the present invention is directed to a method of treating a subject. This method involves identifying a subject in need of treatment and implanting the implantable therapeutic delivery system described herein into the subject to treat the subject.

A further aspect of the present invention is directed to a method of preparing an implantable therapeutic delivery system described herein. This method involves providing a substrate, coating the substrate with a polymer solution, and providing an outer layer of hydrogel comprising one or more therapeutic agents over said coated substrate.

Another aspect of the present invention is directed to an implantable therapeutic delivery system. This therapeutic delivery system comprises a spun substrate and a hydrogel matrix contained within the spun substrate. One or more therapeutic agents are positioned in the hydrogel matrix.

The implantable therapeutic delivery system described herein offers several advantages over currently available implantable encapsulation delivery devices. Compared to macroscopic devices, including both tubular and planar devices, the system described herein has significantly increased surface areas for mass transfer of therapeutic agent to the targeted organ or tissue. Additionally, the diffusion distance is significantly shorter which is beneficial for therapeutic agent delivery. In embodiments involving cell encapsulation for cell-based secretion of the therapeutic agent, this shortened distance is beneficial for cell health. The thin, flexible, yet mechanically robust system of the present inventions is easier to handle and manipulate and enables convenient, non-invasive implantation, retrieval, and replacement of the system. Also, the length of the implantable therapeutic delivery system, unlike many other systems, can be from millimeters to meters.

According to one embodiment, a thread-reinforced alginate fiber for islet encapsulation ("TRAFFIC") system for the treatment of type 1 diabetes is herein described. In one embodiment of this system, a hydrogel fiber provides immuno-protection and high surface area for mass transfer, while a thin, flexible string-like structure imparts mechanical strength and enables easy handling, implantation, and retrieval. A series of studies set forth in the Examples (infra) were conducted to investigate the size effect of the TRAFFIC system to induce/prevent fibrosis. Two groups of TRAFFIC system implants with different diameters were implanted into the intraperitoneal space of C57BL/6 mice (which are known to experience more severe fibrosis than other mouse strains). The results showed that fibrosis did not appear for at least 3 months when larger diameter TRAFFIC system implants (~1.5 mm) were used.

Besides being relatively biocompatible, the system of the present invention has several other advantages compared to currently used islet encapsulation systems or encapsulation of other cell types. The system of the present invention has a large surface area for mass transfer, and it is easy to handle, implant, and retrieve. Unlike other retrievable, macroscopic devices, the system of the present invention has no sealing or leaking issues. Furthermore, the diffusion or mass transfer distance (i.e., the location of islets relative to the surface) can be controlled by adjusting the diameters of the "string" and the hydrogel fiber. A short diffusion distance is not only beneficial for islets survival, but also favored for fast glucose responsiveness. Length is also customizable in the system of the present invention.

As a demonstration of the clinical potential of the system of the present invention, rat islets were encapsulated and obtained a cure of chemically-induced diabetes in mice for at least 1 month at which point all the mice (n=5) remained cured. When removed, the mice returned to their diabetic state. The retrieved systems had moderate cellular overgrowth but functional islets were observed. Finally, to demonstrate that the system of the present invention is a clinically feasible option for T1D patients, the fabrication of the system was scaled up. By using a dog model, such a device was shown that could be conveniently implanted by a minimally invasive laparoscopic procedure, widely dispersed in the peritoneal cavity, and easily retrieved.

BRIEF DESCRIPTION OF THE DRAWINGS

FIGS. 1A-C are schematic representations of one embodiment of an implantable therapeutic delivery system described herein. FIG. 1A is a side view of the implantable system in its entirety. FIG. 1B is a cross-sectional side view along the length of a section of the implantable system, and FIG. 1C is a cross-sectional view taken along lines Z-Z of FIG. 1A.

FIGS. 2A-N relate to one embodiment of an implantable therapeutic delivery system described herein based on a "beads-on-strand" design. FIG. 2A is a schematic illustration of the system. FIG. 2C is an optical microscope image and FIGS. 2D-E are SEM images under different magnifications. FIGS. 2G-H are representative optical microscope images of the implantable therapeutic delivery system with 0.3 mm and 1.5 mm overall diameters. FIGS. 2I-J are hydrogel diameter calibration plots. FIGS. 2K-N are optical/fluorescent microscope images of the implantable therapeutic delivery system with cell aggregates loaded: FIGS. 2K-L are optical/fluorescent microscope images of the implantable therapeutic delivery system loaded with rat pancreatic islets. FIG. 2L is a photograph showing live/dead staining of the rat islets 1 day after encapsulation. FIGS. 2M-N are optical microscope images of the implantable therapeutic delivery system encapsulating human embryonic stem cell-derived pancreatic progenitor cells ("hESCs PPs").

FIGS. 3A-P illustrate size-dependent fibrosis effect of one embodiment of the implantable therapeutic delivery system described herein. FIGS. 3A, B, I, and J are microscope images of a 1.5 mm diameter implantable therapeutic delivery system and FIGS. 3E, F, M, and N are microscope images of a 0.3 mm diameter implantable therapeutic delivery system before implantation (FIGS. 3A, E, I, and M), 14 days (FIGS. 3B and F), and 90 days (FIGS. 3J and N) after implantation. FIGS. 3C, G, K, and O are digital images showing H&E staining of the histology slides of the corresponding retrieved implantable therapeutic delivery systems (FIGS. 3C and 3K show the 1.5 mm diameter system and FIGS. 3G and 3O show the 0.3 mm diameter system). FIGS. 3D, H, L and P are digital images showing immunohistochemistry staining of the corresponding retrieved implantable therapeutic delivery systems (FIGS. 3D and 3L show the 1.5 mm diameter system retrieved at day 14 and 90 after implantation, respectively, and FIGS. 3H and 3P show the 0.3 mm diameter system retrieved at day 14 and 90 after implantation, respectively).

FIGS. 4A-I are digital images showing laparoscopic implantation and retrieval of one embodiment of an implantable therapeutic delivery system described herein in a dog model. FIGS. 4A and D are laparoscopic images of the implantable therapeutic delivery system positioned cranial to the liver during implantation (FIG. 4A) and 15 days after implantation (FIG. 4D). FIGS. 4B and E are microscope images of the implantable therapeutic delivery system before implantation (FIG. 4B) and 15 days after implantation (FIG. 4E). FIGS. 4C and F are digital images showing H&E staining of the histology slides of the implantable therapeutic delivery system before implantation (FIG. 4C) and 15 days after implantation (FIG. 4F). FIG. 4G is a laparoscopic image of the implantable therapeutic delivery system 15 days after implantation, with the arrow showing a break of the hydrogel layer. FIGS. 4H and I are digital images of the retrieved implantable therapeutic delivery system showing a break of the hydrogel layer.

FIGS. 5A-R relate to one embodiment of an implantable therapeutic delivery system based on a "twisted strand" structure. FIG. 5A is a schematic illustration of the structural configuration. FIGS. 5C-E are digital images of bare twisted sutures (FIG. 5C), twisted sutures with polymer coating (FIG. 5D), and a complete implantable therapeutic delivery system (FIG. 5E). FIG. 5F is an SEM image of bare twisted sutures. FIGS. 5G and 5H are SEM images of twisted sutures with a polymer coating. FIGS. 5I-K are fluorescent images of twisted sutures (FIG. 5I), twisted sutures with polymer coating (FIG. 5J), and a complete implantable therapeutic delivery system (FIG. 5K). FIGS. 5L-N are digital images of EDS element mapping of twisted sutures. FIG. 5O is an EDX spectrum of the twisted sutures surface. FIGS. 5P-Q are microscope images of an implantable therapeutic delivery system loaded with human embryonic stem cell derived pancreatic progenitor aggregates (PPs). FIG. 5R is a fluorescent microscope image of live/dead staining of the encapsulated PPs.

FIGS. 6A-H relate to islets encapsulation and an in vivo experiment for type 1 diabetes. FIG. 6A is a schematic illustration of an implantation of rat islets loaded in an implantable therapeutic delivery system in mice. FIG. 6B is a microscope image of the isolated rat pancreatic islets. FIG. 6C is a digital image of a TRAFFIC system containing rat islets (i.e., one embodiment of an implantable therapeutic delivery system described herein) before transplantation. FIG. 6D is a digital image of a TRAFFIC system containing rat islets retrieved from diabetic mice after 1 month. FIGS. 6E-F are digital images of H&E staining of the retrieved a TRAFFIC system containing rat islets histology slide. FIG. 6G is a graph showing blood glucose concentration of 3 STZ-induced diabetic mice and 5 STZ-induced diabetic mice after transplantation of a TRAFFIC system containing rat islets; the devices were retrieved after 4 weeks of implantation. FIG. 6H is a graph of intraperitoneal glucose tolerance tests (IPGTT) in STZ-induced diabetic mice, normal mice, and STZ-induced diabetic mice with a transplantation of a TRAFFIC system containing rat islets.

FIGS. 7A-J relate to laparoscopic implantation and retrieval of an implantable therapeutic delivery system in a dog model. FIG. 7A is a schematic illustration of an implantation of an implantable therapeutic delivery system into a dog model. FIG. 7B is a digital image of the laparoscopic procedure. FIG. 7C is a digital image of the incision wound 4 weeks after implantation. FIG. 7D is a digital image of a retrieved implantable therapeutic delivery system. FIGS. 7E-G are laparoscopic images of the implantable therapeutic delivery system in contact with the liver during transplantation (FIG. 7E) and 4 weeks after transplantation (FIG. 7G). FIGS. 7F and H are microscope images of the implantable therapeutic delivery system before transplantation (FIG. 7F) and after retrieval (FIG. 7H). FIG. 7I is a digital image of H&E staining of the histology slides of the retrieved implantable therapeutic delivery system. FIG. 7J is a series of digital images showing the laparoscopic retrieval process of the implantable therapeutic delivery system.

FIG. 10A is a schematic illustration of the Dynamic Mechanical Analysis (DMA) test. FIG. 10B is a stress-strain curve collected by DMA. As depicted in this graph, the tensile strength of the braided strand alone and braided strand coated with alginate (curves are overlapping in the graph of FIG. 10B) is much greater than the tensile strength of the alginate alone. FIG. 10C is a digital image showing the ease of handling comparing alginate fiber (left image) and an implantable therapeutic delivery system (right image).

FIG. 11A is a beads-on-strand structure, with the arrow pointing to the bare smooth region of the suture. FIG. 11B is a twisted strand structure.

FIGS. 12A-D are 3-D models of two different embodiments of reinforcement strand structures. FIGS. 12A-B are a beads-on-strand design. FIG. 12A shows a 3-D model and FIG. 12B is a section image along the strand axis. FIGS. 12C-D are a twisted strand design. FIG. 12C shows a 3-D model and FIG. 12D is a section image along the strand axis.

FIGS. 16A-F show the fabrication process of a nanofiber-reinforced hydrogel microdevice (NHM) (i.e., one embodiment of an implantable therapeutic delivery system described herein). FIG. 16A is a schematic illustration of the electrospinning process on a rotating template. FIG. 16B is a schematic illustration of the automatic crosslinking process of an alginate hydrogel by $Ca^{2+}$-releasing nanofibers. FIGS. 16C-E are fluorescent microscope images showing the components of the NHM including the nylon nanofibers (FIG. 16C; labeled in red), and the alginate hydrogel (FIG. 16D, labeled in green). FIG. 16E is a merged image showing the nylon nanofibers and alginate hydrogel. FIG. 16F is a schematic illustration of multi-compartmental NHM devices.

FIGS. 17A-D provide characterizations of NHM devices. FIG. 17A are digital images of the electrospun nylon nanofiber devices with different sizes or capacities (top) and multi-microcompartments (bottom). FIG. 17B is an SEM image of a nanofibrous micropackage with the inset showing the open end. FIG. 17C is an SEM image of a freeze-dried NHM device wall. The insets show a digital image of the NHM device (top) and a confocal image of the cross section of the NHM device (bottom, red: nanofibers, green: alginate). FIG. 17D is a graph showing the strain-stress curves of the electrospun nylon nanofiber sheet, alginate hydrogel sheet, and nanofiber-reinforced alginate hydrogel sheet. The insets of FIG. 17D are digital pictures of the test samples.

FIGS. 18A-I depict in vitro cell encapsulation and culture using the NHM devices. FIGS. 18A and 18B are images of encapsulated MDA-MB-231 cells stained with calcium-AM (green, live) and ethidium homodimer (red, dead) day 0 (FIG. 18A) and 5 days after encapsulation (FIG. 18B). FIG. 18C is a growth curve of the encapsulated MDA-MB-231 cells by MTT analysis (mean±s.d., n=3). FIG. 18D is a fluorescent image of the encapsulated islets stained with calcium-AM (green, live) and ethidium homodimer (red, dead). FIG. 18E is an image of immunohistochemical staining of the encapsulated islets (green: insulin, blue: nuclei). FIG. 18F is a graph showing glucose stimulated insulin secretion of the islets encapsulated in the NHM (mean±s.d., n=3). FIGS. 18G-18I are images of the MDA-MB-231-EGFP (green) and MDA-MB-231-dTomato (red) cells encapsulated in a compartmentalized NHM device. FIG. 18G is a fluorescent microscope image. The inset of FIG. 18G provides an illustration of the cross-section of the device. FIG. 18H is a confocal image of the encapsulated cells at a higher magnification, and FIG. 18I is a three-dimensional fluorescent image showing the localization of the encapsulated cells.

FIGS. 19A-E show in vivo cell delivery using NHM devices. FIG. 19A is a graph showing blood glucose data of STZ-induced diabetic mice after the transplantation of encapsulated rat islets; the NHM devices were retrieved after 8 weeks of implantation (mean±s.d., n=3). FIG. 19B is a representative digital image of the retrieved devices. FIG. 19C is a histology analysis of the retrieved devices. Sections were stained with H&E and observed under a light microscope. FIG. 19D is a magnified image of the wall of the retrieved device shown in FIG. 19C, where the nanofibers, alginate hydrogel, and cellular overgrowth are indicated by arrows. A representative image of immunohistochemical staining of the encapsulated islets in the retrieved devices is depicted in FIG. 19E (green: insulin, blue: nuclei).

FIGS. 20A-J is a panel of microscope images and digital images of various electrospun nanofibers and nanofiber (tubular) micropackages including the nylon 6 fibers (FIGS. 20A-B), polyacrylonitrile (FIGS. 20C-D), polycaprolactone (FIGS. 20E-F), polysulfone (FIGS. 20G-H), and polystyrene (FIGS. 20I-J)

FIGS. 21A-D are microscope images and digital images of the nylon 6 nanofiber-reinforced alginate hydrogel (FIGS. 21A-B) and poly(ethylene glycol) diacrylate (PEGDA) hydrogel (FIGS. 21C-D) microdevices. The location of the hydrogel is indicated by the arrows.

DETAILED DESCRIPTION OF THE INVENTION

Figure 2A:

A first aspect of the present invention is directed to an implantable therapeutic delivery system. This therapeutic delivery system comprises a substrate, an inner polymeric coating that surrounds the substrate, and an outer hydrogel coating that surrounds said inner polymeric coating. One or more therapeutic agents are positioned in the outer hydrogel coating.

FIGS. 1A-1C are schematic representations of one embodiment of an implantable therapeutic delivery system of the present invention. As shown in FIG. 1A, the implantable therapeutic delivery system 10 has a thin, flexible strand or string-like design. This design is advantageous because it provides increased surface area for transfer and delivery of a therapeutic agent encapsulated within the device as described herein, and is easy to handle, implant, and retrieve. The implantable system 10 can be any desired length within the range of millimeters to meters and will vary depending on targeted region of delivery as well as the amount of therapeutic agent to be delivered and the size of the implant recipient. For example, in one embodiment, the implantable system 10 is about 10, 20, 30, 40, 50, 60, 70, 80, 90, or 100 millimeters in length. In another embodiment, the implantable system 10 is about 20, 30, 40, 50, 60, 70, 80, 90, or 100 cm in length. In another embodiment, the implantable system is greater than 100 cm in length.

The diameter of the implantable system is generally in the range of microns to centimeters. In one embodiment the diameter of the implantable system is <50 microns in diameter. In another embodiment the diameter of the implantable system is 50, 100, 200, 300, 400, 500, 600, 700, 800, 900 µm. In another embodiment, the implantable system is 1, 1.5, 2, 2.5, 3, 3.5, 4, 4.5, 5, 5.5, 6, 6.5, 7, 7.5, 8, 8.5, 9, 9.5, or 10 mm. In another embodiment the diameter of the implantable system is >10 mm. When the implantable system contains cells in the outer hydrogel layer, the optimal diameter of the implantable system described herein may be controlled by oxygen requirements of the cells, i.e., the diameter must be small enough to allow adequate oxygen diffusion to the cells dispersed in the hydrogel layer to avoid hypoxia. However, when the implantable system comprises one or more internal fluidic spaces that serve as an oxygen reservoir as described infra, the diameter of the system may be larger.

FIG. 1B is a cross-sectional view along the length of a portion of the implantable system of FIG. 1A, and FIG. 1C is a cross-sectional view taken along lines Z-Z of FIG. 1A. As depicted in these figures, the core of the implantable system comprises a substrate 12. In one embodiment, the substrate is a single elongate strand (see e.g., FIG. 2A). In another embodiment, the substrate comprises two or more elongate strands twisted or braided together to form a twisted elongate strand (see e.g., FIG. 5A). In accordance with this embodiment, the substrate may comprise 2, 3, 4, 5, 6, 7, 8, 9, 10 or more elongate strands twisted together. The elongate strands are comprised of a flexible, solid, or semi-solid material. In one embodiment the substrate contains one or more internal fluidic spaces. The one or more internal fluidic spaces can be of any configuration. For example, in one embodiment, the substrate comprises a single internal fluidic space configured as a single hollow tube. In another embodiment, the substrate comprises an internal fluidic space configured as a hollow tube, a compartmentalized hollow tube, or two or more hollow tubes. In yet another embodiment, the internal fluidic spaces are contiguous spaces distributed throughout a semi-solid substrate matrix. The substrate may comprise a gas impermeable, semi-permeable, or permeable material. The substrate may also comprise a liquid impermeable, semi-permeable, or permeable material. In one embodiment, the substrate comprises one or more elongate strands comprised of a flexible semi-solid gas permeable, liquid impermeable material, with one or more internal fluidic spaces. The internal fluidic spaces serve as a reservoir for one or more biological agents, such as, for example, oxygen as described in more detail infra. The substrate runs the length of the implantable system and comprises a diameter of between about 1 µm to about 25 mm.

Suitable substrate materials include materials that are insoluble in the polymeric coating (described infra) which surrounds the substrate. Suitable substrate materials include, for example, and without limitation, synthetic or natural fibers comprised of nylon, silk (e.g., spider silk and silkworm), poly(ether sulfone), polypropylene, polyester, polybutester. The substrate may also comprise nanofibers of natural polymers, e.g., gelatin, chitosan, hyaluronic acid, silk fibroin, and collagen, or synthetic polymers, e.g., poly (lactic acid) (PLA), polyurethane (PU), polycarbonate (PC), polyethylene (PE), polydimethylsiloxane (PDMS), polymethylmethacrylate (PMMA), poly(ε-caprolactone) (PCL), poly(lactic-co-glycolic acid) (PLGA), poly(ethylene-co-vinylacetate) (PEVA), and poly(1-lactide-co-ε-caprolactone) (PLLA-CL). To enhance the tensile strength of the substrate material, it may be reinforced with graphene or carbon nanotubes (see, e.g., U.S. Patent Publication No. 20070082197 to Ko, which is hereby incorporated by reference in its entirety).

As illustrated in FIGS. 1B and 1C, an inner polymeric coating 14 surrounds the substrate 12. In one embodiment, the polymeric coating is porous and permeable, e.g., gas permeable and/or liquid permeable. In another embodiment, the polymeric coating is gas and/or liquid impermeable. The polymeric coating comprises a material that is compatible with the substrate material, i.e., the polymeric coating is comprised of a material that does not dissolve the substrate material, and is different than the substrate material. Suitable polymeric coatings include relatively hydrophilic and water insoluble polymers such as, for example and without limitation, poly(methyl methacrylate), polyacrylonitrile, poly(lactic acid) (PLA), polyurethane (PU), polycarbonate (PC), polyethylene (PE), polydimethylsiloxane (PDMS), poly(ε-caprolactone) (PCL), poly(lactic-co-glycolic acid) (PLGA), poly(ethylene-co-vinylacetate) (PEVA), poly(1-lactide-co-ε-caprolactone) (PLLA-CL), and any combination of these or other polymers.

In one embodiment, the polymeric coating contains and releases cationic cross-linking agents suitable for crosslinking the polymeric coating to the outer hydrogel layer (described infra) of the implantable therapeutic delivery system. In one embodiment, the cationic cross-linking agents are divalent cations such as $Ba^{2+}$, $Ca^{2+}$, $Cd^{2+}$, $Cu^{2+}$, $Fe^{2+}$, $Mg^{2+}$, $Mn^{2+}$, $Ni^{2+}$, $Pb^{2+}$, $Sn^{2+}$, $Sr^{2+}$, and $Zn^{2+}$. In one embodiment, the divalent cross-linking agent is calcium chloride. Other suitable cationic cross-linking agents include, without limitation, $Al^{3+}$ and $Fe^{3+}$. The cross-linking agent is present in the polymeric coating at a concentration sufficient to cross-link and adhere the outer hydrogel layer, e.g., >0.5% of the polymeric coating solution. Accordingly, in some embodiments, the cross-linking agent is present in an excess concentration, e.g., >2%. A suitable concentration of cross-linking agent is between 1-20%.

The solvent used for making the polymeric coating material is any organic solvent that dissolves and/or disperses the crosslinking agent of the polymer coating, but does not cause dissolution of the substrate. Suitable organic solvents are those with low surface tension, including, for example, and without limitation, dichloromethane, N,N-dimethyl formamide, ethanol, methanol, or any combination thereof. The ratio of polymer-to-solvent varies depending on for example, which polymer-solvent combination is utilized, as well as the polymer weight. However, generally, the polymer comprises 1-40% of the coating solution, i.e., the polymer comprises about 1%, 5%, 10%, 15%, 20%, 25%, 30%, 35%, 40% of the coating solution. In another embodiment, the polymer comprises >40% of the polymer coating solution.

In one embodiment, the polymeric coating forms separate anchoring particles or beads along the length of the substrate during the drying process due to surface tension driven by Rayleigh instability (see, e.g., FIG. 2A). In one embodiment, the beads or particles have an oval, slightly elongated shape with a transverse diameter of about 100-300 µm. The beads are highly porous and provide increased surface area for cross-linking agent release, which in turn may improve the adhesion between the coated substrate and the outer hydrogel layer.

As illustrated in FIGS. 1B and 1C, an outer hydrogel coating 16 surrounds the inner polymeric coating 14. This hydrogel layer 16 contains one or more therapeutic agents 18 as part of the implantable therapeutic delivery system 10.

The hydrogel coating is comprised of a material that cross-links with the inner polymeric coating. Suitable hydrogel materials include natural and synthetic polymeric materials. The hydrogel coating can be homopolymeric, copolymeric, or multipolymeric in composition. Suitable hydrogel materials include, without limitation, those derived from collagen, hyaluronate, fibrin, alginate, agarose, chitosan, bacterial cellulose, elastin, keratin, MATRIGEL™, DNA (as a true polymer), and combinations thereof. In other embodiments, suitable hydrogels are synthetic polymers including those derived from polyethylene glycol (PEG), poly(acrylic acid) and derivatives thereof, poly(ethylene oxide) and copolymers thereof, poly(vinyl alcohol), polyphosphazene, and combinations thereof.

Other biocompatible materials that are suitable for outer coatings of the implantable system described herein include anisotropic materials, polysulfone (PSF), nano-fiber mats, polyimide, tetrafluoroethylene/polytetrafluoroethylene (PTFE; also known as Teflon™), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes.

As depicted in FIGS. 1B and 1C, the therapeutic agent 18 of the implantable therapeutic delivery system 10 is positioned within and distributed throughout the outer hydrogel coating 16 along the entire length of the implantable system 10. The therapeutic agent can be any biologically reactive agent including, for example, and without limitation, therapeutic proteins, peptides, antibodies or fragments thereof, antibody mimetics, and other binding molecules, nucleic acids, small molecules, hormones, growth factors, angiogenic factors, cytokines, and anti-inflammatory agents.

The types of drugs (or therapeutic agents) that can be delivered using the implantable delivery system described herein are numerous, and include both small molecular weight compounds in the size range from 100 daltons to about 1,000 daltons as well as the larger macromolecular drugs, such as peptide and protein drugs in the size range from about 1,000 daltons to about 100,000 daltons, and beyond. The system is particularly well suited to deliver drugs having relatively low effective doses, e.g., in the micrograms/day, nanograms/day, and even picograms/day range.

Protein and/or peptide therapeutic agents which may be contained within the implantable system for delivery upon implantation in a subject include, without limitation, peptide hormones such as insulin, glucagon, parathyroid hormone, calcitonin, vasopression, renin, prolactin, growth hormone, the gonadotropins, including chorionic gonadotropin, follicle stimulating hormone, thyroid stimulating hormone, and luteinizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, platelet-derived growth factors, erythropoietin, colony stimulating factors, bone morphogenetic proteins, interleukins, and interferons. Non-protein macromolecules, particularly including polysaccharides, nucleic acid polymers, and therapeutic secondary metabolites, including plant products such as vinblastine, vincristine, taxol, and the like may also be delivered using the present system. Small molecular weight compounds may also be delivered.

In one embodiment, the therapeutic agent is a biological agent produced and/or secreted or released from tissue and/or a preparation of cells encapsulated within or residing within the outer hydrogel layer of the implantable system. The cells may comprise naturally occurring or genetically engineered cells which may be in the form of single cells and/or cell clusters. In one embodiment, the cells within the hydrogel outer layer of the implantable system secrete one or more biological factors that are useful in the treatment of a disease or condition. These factors are secreted from the cells, released from the hydrogel layer, and are delivered to or diffuse to surrounding target cells, tissue, or organ in need thereof. Suitable cells include, without limitation, one or more cell types selected from the group consisting of smooth muscle cells, cardiac myocytes, platelets, epithelial cells, endothelial cells, urothelial cells, fibroblasts, embryonic fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, embryonic stem cells, mesenchymal stem cells, neural cells, endothelial progenitor cells, hematopoietic cells, and precursor cells.

In one embodiment, the cells are insulin secreting cells, such as pancreatic islet cells.

As noted above, suitable cells include progenitor and/or stem cells. Suitable stem cells may be pluripotent, multipotent, oligopotent, or unipotent cells or cell populations, and include embryonic stem cells, epiblast cells, primitive ectoderm cells, and primordial germ cells. In another embodiment, suitable stem cells also include induced pluripotent stem (iPS) cells, which are pluripotent stem cells derived from a non-pluripotent cell. See Zhou et al., *Cell Stem Cell* 4:381-384 (2009); Yu et al., *Science* 324(5928):797-801 (2009); Yu et al., *Science* 318(5858):1917-20 (2007); Takahashi et al., *Cell* 131:861-72 (2007); and Takahashi and Yamanaka, *Cell* 126:663-76 (2006), which are hereby incorporated by reference in their entirety. In accordance with this embodiment, the hydrogel layer may further comprise the growth and differentiation factors suitable for promoting stem cell differentiation into a desired population of cells capable of producing and releasing the therapeutic agent of interest.

Suitable cells for encapsulation in the implantable system described herein can be derived from any animal capable of generating the desired cells. The animals from which the cells are harvested may be vertebrate or invertebrate, mammalian or non-mammalian, human or non-human. Examples of animal sources include, but are not limited to, primate, rodent, canine, feline, equine, bovine, or porcine. The cells may be obtained from or comprise a primary cell preparation or immortalized cells preparations. The encapsulated cells may be isolated from the same species as the implant recipient or from a different species than the implant recipient.

In some embodiments, the system described herein comprises a cell density between approximately $1 \times 10^5$ or $1 \times 10^6$ cells/ml to about $1 \times 10^{10}$ cells/mL or more. In one embodiment, the cell holding capacity of the system is based, at least in part, on the length of the system. The cells are capable of surviving in vivo in the implantable system for at least a month, two months, three months, four months, five months, six months, seven months, eight months, nine months, ten months, eleven months, twelve months or a year or more with a functionality that represents at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more of the function expressed at the time the cells are/were introduced into the system or at the time the cells fully develop and/or mature in the system, e.g., implantation of progenitor cells which need to further develop or mature to functional cells in vivo. In some embodiments, the cells or cell preparation in the system expand within the system to increase cell density and/or cell function upon implantation of the system in vivo.

When the outer hydrogel coating of the system contains cells or a cell preparation, additional cell specific growth and/or differentiation factors may be added to the hydrogel solution to enhance cell growth, differentiation, and survival. These factors include supplements (e.g., glutamine, non-essential amino acids), growth factors (e.g., epidermal growth factors, fibroblast growth factors, transforming growth factor/bone morphogenetic proteins, platelet derived growth factors, insulin growth factors, cytokines), extracellular matrix proteins (e.g., fibronectin, laminin, heparin, collagen, glycosaminoglycan, proteoglycan, elastin, chitin derivatives, fibrin, and fibrinogen), angiogenic factors (e.g., FGF, bFGF, acid FGF (aFGF), FGF-2, FGF-4, EGF, PDGF, TGF-beta, angiopoietin-1, angiopoietin-2, placental growth factor (PlGF), VEGF, and PMA (phorbol 12-myristate 13-acetate)), and signaling factors and/or transcription factors.

One obstacle to the field of cell and tissue encapsulation/immuno-isolation has been the lack of sufficient oxygen and nutrient transport across the polymer membranes used to encapsulate cells and tissues. The result of this insufficient gas and nutrient exchange is lowered metabolic activity and cell death. Accordingly, in one embodiment, the implantable system comprises a configuration designed to include an oxygen source that is readily available to the encapsulated cells or tissues and/or biologically active agents. For example, as described supra, the substrate of the implantable system may comprise one or more internal fluidic spaces that serve as an oxygen reservoir. Suitable oxygen carriers that can be contained within the internal spaces of the substrate include perfluoro organic compounds, e.g., perfluorocarbons ("PFCs"), a PFC-emulsion, or mixture of PFC with some matrix. PFCs are good oxygen carriers because they have several fold higher solubility for oxygen than water. For example, under normal conditions, liquid PFCs dissolve between 40% and 55% by volume of oxygen and between 100% and 150% by volume of $CO_2$. PFC derivatives are dense, chemically inert, and water insoluble compounds that cannot be metabolized.

Suitable PFC substances include, but are not limited to, perfluorotributylamine (FC-43), perfluorodecalin, perfluorooctyl bromide, bis-perfluorobutyl-ethene, perfluoro-4-methylmorpholine, perfluorotriethylamine, perfluoro-2-ethyltetrahydrofuran, perfluoro-2-butyltetrahydrofuran, perfluoropentane, perfluoro-2-methylpentane, perfluorohexane, perfluoro-4-isopropylmorpholine, perfluorodibutyl ether, perfluoroheptane, perfluorooctane, and mixtures thereof. Preferred inert fluorochemical liquids include perfluorohexane, perfluoro-2-butyltetrahydrofuran, perfluoroheptane, perfluorooctane, and mixtures thereof. Commercially available PFCs useful in the embodiments herein include FLUORINERT™ fluids, e.g., FC-72, FC-75, FC-77, and FC-84, described in the 1990 product bulletin #98-0211-5347-7(101.5) NPI, FLUORINERT™ fluids, (available from Minnesota Mining and Manufacturing Company, St. Paul, Minn.), and mixtures thereof.

The outer hydrogel layer of the implantable system may further comprise one or more anti-inflammatory reagents that help reduce and/or eliminate a host inflammatory or fibrotic response to the implanted device. Suitable anti-inflammatory agents include, without limitation, non-steroidal anti-inflammatory drugs (NSAID) (e.g., diclofenac, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, salsalate, sulindac, and tolmetin), analgesics (e.g., acetaminophen, oxycodone, tramadol, and propoxyphene hydrochloride), glucocorticoids (e.g., cortisone, dexamethasone, hydrocortisone, methylprednisolone, prednisolone, and prednisone), and dihydrofolate reductase inhibitors (e.g., methotrexate).

In another embodiment, the implantable system described herein comprises one or more contrast agents to facilitate in vivo monitoring of implant placement, location of implant at some time point after implantation, health of the implant, deleterious effects on non-target cell types, inflammation, and/or fibrosis. Suitable contrast agents include, without limitation, nanoparticles, nanocrystals, gadolinium, iron oxide, iron platinum, manganese, iodine, barium, microbubbles, fluorescent dyes, and others known to those of skill in the art.

Methods of in vivo monitoring include but are not limited to confocal microscopy, 2-photon microscopy, high frequency ultrasound, optical coherence tomography (OCT), photoacoustic tomography (PAT), computed tomography (CT), magnetic resonance imaging (MRI), single photon emission computed tomography (SPECT), and positron emission tomography (PET). These alone or combined can provide useful means to monitoring the implantable system.

In another embodiment, the therapeutic agent is produced by and/or released from the system described herein by a bio- or nano-biochip encapsulated within or residing within the outer hydrogel layer of the implantable system. For example, the biochip or nano-biochip device may implement semiconductor and/or micro-electro-mechanical systems technologies for use in providing therapeutic regiments for various human diseases (see, e.g., U.S. Patent Application Publication No. 2013/0345525 to Kline, which is hereby incorporated by reference in its entirety).

Another aspect of the present invention is directed to an alternative configuration of the implantable therapeutic delivery system. This therapeutic delivery system comprises a nanofibrous core substrate having one or more internal spaces suitable for compartmental encapsulation of one more types of cells, cell preparations, or therapeutic agents. An outer biocompatible polymeric coating surrounds the nanofibrous substrate of this system.

Suitable substrate materials include, without limitation, the natural and synthetic materials as described supra. However, in accordance with this embodiment, the substrate of this aspect of the present invention contains and releases a cross-linking agent that is suitable for facilitating cross-linking between the substrate material and the outer biocompatible polymeric coating. Suitable cross-linking agents are described supra. In some embodiments, the substrate material further contains one or more biologically reactive reagents, such as, e.g., anti-inflammatory reagents that are slowly release to mitigate any host immune system inflammatory response and fibrosis. Alternatively, the substrate material may contain and release one or more therapeutically active reagents.

The encapsulated cells according to this aspect of the present invention can be in the form of single cells or cell aggregates, and can be derived from any of the suitable sources described supra. Likewise, the cells or cell preparations may comprise primary cells, immortalized cells, genetically engineered cells, and the like. Suitable cell types, including stem and progenitor cells types, are described supra.

The encapsulated cells are loaded into this system in a custom designed manner, i.e., with a controlled extracellular matrix and space, i.e., cell specific environmental factors and conditions can be incorporated into this system to enhance cell survival, growth, proliferation, differentiation, and function when necessary. This design feature greatly enhances the implanted cells' health and overall lifespan.

The outer biocompatible polymeric coating of the system of this aspect is comprised of a hydrogel material. In one embodiment, the hydrogel is made from an ultra-compatible, chemically modified alginate. In another embodiment, the hydrogel is made from a photo-crosslinkable polyethylene glycol. In yet another embodiment, the hydrogel is made of a foreign body response-resistant zwitterionic polymer. In some embodiments, one or more therapeutic agents are positioned in the outer hydrogel coating.

Other aspects of the present invention relate to treatment methods that involve implanting the therapeutic system into a subject to be treated. Thus, another aspect of the present invention is directed to a method of delivering a therapeutic agent to a subject. This method involves implanting the implantable therapeutic delivery system described herein into a subject. A further aspect of the present invention is directed to a method of treating a subject. This method involves implanting the implantable therapeutic delivery system described herein into a subject having a condition or disease. Suitable conditions or diseases for treatment using the implantable therapeutic delivery system include, inter alia, chronic conditions or disease states requiring long term repeated administration of a therapeutic agent. In one embodiment, the condition is diabetes which requires ongoing insulin therapy.

The implantable system described herein can be employed for treating a variety of diseases and conditions requiring a continuous supply of biologically active substances to the organism. The system may contain homogenous or heterogenous mixtures of biologically active agents and/or cells, or cells producing one or more biologically active substances of interest. The biologically active agents and/or cells are wholly encapsulated within the outer semi-permeable hydrogel layer. Such a semi-permeable outer layer allows the encapsulated biologically active substance of interest (e.g., insulin, glucagon, pancreatic polypeptide, and the like in the case of treating diabetes) to pass out of the system, making the active substance available to target cells outside the system and in the recipient subject's body. In one embodiment, the semi-permeable membrane allows nutrients naturally present in the subject to pass through the membrane to provide essential nutrients to cells present in the hydrogel. At the same time, such a semi-permeable membrane prevents the recipient subject's cells, more particularly, their immune system cells, from passing through and into the implantable system to harm the cells in the system. For example, in the case of diabetes, this approach can allow glucose and oxygen (e.g., contained within the body) to stimulate insulin-producing cells of the implant system to release insulin as required by the body in real time while preventing host immune system cells from recognizing and destroying the implanted cells.

In one embodiment, the semi-permeable membrane prohibits cells in the hydrogel from escaping the implantable system.

The implantable system can be surgically implanted into subjects. In one embodiment, the system is implanted using minimally invasive surgical techniques such as laparoscopy. The system can be implanted percutaneously, subcutaneously, intraperitoneally, intrathoracically, intramuscularly, intraarticularly, intraocularly, or intracerebrally depending on the therapeutic agent being delivered, condition to be treated, and tissue or organ targeted for delivery.

In one embodiment, the implantable system is anchored or immobilized (e.g., by suture) at the implantation site to maintain the system and/or the released therapeutic agent at or near the implantation site. In one embodiment, the anchor site is at or close in proximity to, a tissue or organ which is the focus of the treatment. In other embodiments where delivery of the therapeutic agent from the system is not location dependent and biodistribution of the agent is dependent on the subject's vasculature or body fluids, the system can be implanted and anchored in a remote location. In one embodiment, the implantable delivery system is implanted percutaneously or subcutaneously under the skin on the abdomen, forearm, flank, back, buttocks, leg, and the like, where it substantially remains until such time as it is required to be removed.

In one embodiment, the implantable system is retrievable after implantation. Anchoring or immobilizing the system as described supra prevents the system from migrating, moving, or traversing inside the patient and facilitates easy retrieval. In accordance with this embodiment, the system may further comprise a tether that aids in retrieval. Retrieval is desirable after release of the therapeutic agent in its entirety or, in an embodiment where the implantable system contains cells, when the cells cease to release adequate amounts of therapeutic agent. Following retrieval, the retrieved system can be replaced by another system to maintain therapeutic agent delivery in the subject. A second or subsequently implanted system can be implanted in the same or a different location.

The implantable therapeutic delivery system described herein provides several advantages over other cell encapsulation techniques developed for the delivery of insulin secreting cells for the treatment of diabetes. The primary advantage is that cell dispersion in the outer hydrogel layer of the implantable system creates a short diffusion distance which affords fast glucose responsiveness. The short diffusion distance also enhances nutrient and oxygen delivery to the islet cells within the system thereby greatly improving long term islet cell survival and functionality.

The implantable system containing insulin producing and secreting cells (e.g., islet cells) is suitable for treating a subject having Type I (juvenile diabetes) or Type II diabetes. Suitable subjects include children, adults, and elderly subjects having an insulin deficiency.

In accordance with one embodiment, the implantable system containing insulin producing cells is implanted laparoscopically into the abdominal cavity or thoracic cavity. Utilization of the implantable system by a diabetic patient will substantially decrease the need to monitor blood sugar levels and may eliminate the need for insulin injections altogether. The implanted system may be monitored regularly (e.g., monthly or bi-monthly) to ensure the cells of the implant are functioning adequately.

In accordance with the aspect of the invention directed to treatment of diabetes, the implantable system comprises insulin producing cells. Suitable insulin secreting cells include islet cells. Since the cells within the implantable system described herein are protected from the host immune system, the islet cells can be derived from any suitable source, i.e., human or non-human. Examples of suitable animal sources include, without limitation, primates, pigs, bovids, equids, felids, canids, and rodents. In one embodiment, the islet cells are stem or progenitor cells, including induced pluripotent stem cells that differentiate into insulin producing islet cells. Suitable insulin secreting cell populations and methods for producing such populations are known in the art, see, e.g., and without limitation, U.S. Pat. No. 8,425,928 to Martinson et al.; U.S. Pat. Nos. 5,773,255 and 5,712,159 to Fiore; U.S. Pat. No. 6,642,003 to Perfetti et al.; Rezania et al., "Reversal of Diabetes with Insulin-Producing Cells Derived In vitro from Human Pluripotent Stem Cells," *Nat. Biotech.* 32:1121-1133 (2014); Kuo et al., "Stem Cell Therapy: Differentiation Potential of Insulin Producing Cells from Human Adipose Derived Stem Cells and Umbilical Cord MSCs," *Int'l J. Clin. Med.* 1(1):21-25 (2014); Thakkar et al., "Insulin-secreting Adipose-derived Mesenchymal Stromal Cells with Bone Marrow-derived Hematopoietic Stem Cells from Autologous and Allogenic Sources for Type I Diabetes Mellitus," *Cytotherapy* doi.org/10.1016/j.jcyt.2015.03.608 (pub. Online April 2015), which are hereby incorporated by reference in their entirety.

Another aspect of the present invention is directed to a method of preparing the implantable therapeutic delivery system described herein. This method involves providing a substrate, coating the substrate with a polymer solution, and providing an outer layer of hydrogel comprising one or more therapeutic agents over said coated substrate.

Exemplary methods of preparing the implantable therapeutic delivery system of the present invention are described in the Examples below. These processes are simple and benign and do not require the use of microfabricated devices or complicated apparatuses such as droplet-generators for microcapsule production.

The process begins with coating the substrate, i.e., one or more thin, flexible, mechanically stable, strings or strands, with a polymeric material that does not dissolve the substrate. Suitable substrate materials and configurations are described supra.

The polymeric coating forms a thin coating over the substrate, and in some embodiments, forms separate "anchoring" beads or particles along the string. In this and all embodiments, the polymeric coating is contiguous along the length of the substrate. The process of coating the substrate with the polymeric material, e.g., by dipping or immersing the substrate into the polymeric solution, can be repeated one or more times to increase the thickness of the polymeric coating, which in turn will enhance the mechanical strength and size of the resulting system. The polymeric coating contains divalent cations or other cross-linking agents as described supra. A crosslinking agent is important for internal crosslinking between the polymeric coating and the outer hydrogel layer. The concentration of the cross-linking agents can be modified, i.e., increased or decreased, as a means of controlling the diameter of the implantable system.

The polymeric coated substrate is then immersed in a hydrogel solution to form the outer biocompatible layer of the implantable system. The immersion time of the substrate in the hydrogel solution can vary between 1-60 minutes or more, and provides another means of controlling the diameter of the implantable system, i.e., the longer the immersion time, the larger the diameter of the outer hydrogel layer.

A therapeutic agent of interest or cells producing or secreting the therapeutic agent of interest may be, according to one embodiment, distributed throughout the hydrogel material prior to or during the process of coating the polymeric coated substrate. The concentration of the therapeutic agent or cell density within the hydrogel layer will vary depending on the condition and individual being treated and can readily be determined and/or adjusted by one of skill in the art.

In some embodiments, the hydrogel coated system is further cross-linked by exposure to a second, external cross-linking agent, e.g., $CaCl_2$, $BaCl_2$, or any of the crosslinking agents disclosed supra.

To fabricate the cell-loaded system of the present invention, according to one embodiment, a thin suture is first coated with a highly porous, $Ca^{2+}$-releasing polymeric layer. The modified suture is then submerged in a cell-containing alginate solution where the crosslinking occurs around the modified suture in situ due to $Ca^{2+}$ release. The size of the hydrogel fiber can be controlled by adjusting the $Ca^{2+}$ content of the polymeric layer and the submerging time. The hydrogel fiber may be further crosslinked using an external $Ba^{2+}$ solution. The whole fabrication process is simple and benign, and does not involve microfabricated devices or complicated apparatuses such as droplet-generators for microcapsule production. The modified fiber can be pre-made and supplied as an "off-the-shelf," easy-to-use platform for research and clinical communities.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

EXAMPLES

The following examples are provided to illustrate embodiments of the present invention but they are by no means intended to limit its scope.

Example 1—A Thread-Reinforced Alginate Fiber for Islet Encapsulation Materials and Methods Chemicals. Calcium chloride ($CaCl_2$), barium chloride ($BaCl_2$), sodium chloride (NaCl), poly(methyl methacrylate) (PMMA), and N,N-dimethylformamide (DMF) were purchased from Sigma-Aldrich Co. (St. Louis, MO). Glucose was purchased from Mallinckrodt Pharmaceuticals (Dublin, Ireland). Sodium alginate was purchased from FMC BioPolymer Co. (Philadelphia, PA). All chemicals were used without further purification. Water was deionized to 18.2 MΩ-cm with a Millipore purification system.

Animals. C57BL/6 mice for implantation experiments were obtained from The Jackson Laboratory (Bar Harbor, ME). Sprague-Dawley rats for isolation of pancreatic islet cells were obtained from Charles River Laboratories (Wilmington, MA). Beagle dogs for implantation were obtained from Marshall Bioresources (Clyde, NY). All animal procedures were approved by the Cornell Institutional Animal Care and Use Committee.

Characterizations. The samples were characterized by different analytical techniques. Scanning electron microscopy (SEM) and energy dispersive spectrometer (EDS) element mapping were performed by using a field emission scanning electron micro-analyzer (LEO 1550). Optical and fluorescent microscopic images were observed by a digital inverted microscope (EVOS fl). Conventional macro-tensile measurements were performed using a dynamic mechanical analysis (DMA Q800). All samples were mounted between holders at a distance of ~1.5 cm. Tensile testing was conducted at a rate of 0.5 N/min at room temperature (23° C.). Stress (MPa) and strain (%) were automatically calculated by the software. Confocal images were taken by using a Laser Scanning Confocal Microscope (LSM 710).

Fabrication of Modified Sutures. Typically, for the beads-on-a-strand design, a suture (Ethilon Nylon Suture, 3-0, monofilament, Ethicon, Inc.) was first fixed tightly on a holder. The suture was submerged into a 7% (w/v) PMMA/DMF solution containing 2.5% (w/v) $CaCl_2$, for 3 seconds. The suture was then taken out from the polymer solution and dried in air. For the helical suture design, a sterile 5-0, monofilament nylon suture (Ethilon Nylon Suture, Ethicon, Inc.) was used. After the modification was finished, all the sutures were sterilized by Gamma-Radiation before use.

Rat Islet Isolation and Purification. Sprague-Dawley rats from Charles River Laboratories weighing approximately 300 g were used for harvesting islets. All rats were anesthetized using 3% isoflurane in oxygen and maintained at the same rate throughout the procedure. Isolation surgeries were performed as described by Lacy and Kostianovsky, "A Method for the Isolation of Intact Islets of Langerhans from the Rat Pancreas," *Diabetes* 16:35 (1967), which is hereby incorporated by reference in its entirety. Briefly, the bile duct was cannulated and the pancreas was distended by an in vivo injection of 0.15% Liberase (Research Grade, Roche) in RPMI 1640 media solution. The pancreas was digested in a 37° C. water bath for 30 min. The digestion was stopped by adding 10-15 mL of cold M199 media with 10% heat-inactivated fetal bovine serum and a slight shaking. Digested pancreases were washed twice in M199 media, filtered through a 450 mm sieve, and then suspended in a Histopaque 1077 (Sigma)/M199 media gradient and centrifuged at 1700 RCF at 4° C. This gradient centrifugation step was repeated for higher purity islets. Finally, the islets were collected from the gradient and further isolated by a series of gravity sedimentations, in which each supernatant was discarded after 4 min of settling. Purified islets were hand-counted by aliquot under a light microscope and then washed three times in sterile PBS. Islets were then washed once in RPMI 1640 media with 10% heat-inactivated fetal bovine serum and 1% penicillin/streptomycin, and cultured in this medium overnight for further use.

Cell Encapsulation. Typically, the desired cell density was pre-calculated. Cells were dispersed in pre-determined volume of 2% (w/v) sodium alginate solution (SLG100). Then the modified suture was submerged into the cell-loaded alginate solution for 4 min. After removal from the alginate solution, the attached hydrogel layer was further crosslinked by a crosslinking buffer containing 100 mM $CaCl_2$ and 5 mM $BaCl_2$. Next, the device was washed three times with 9% (w/v) saline and put into corresponding cell culture medium. For islet encapsulation, immediately prior to encapsulation, the cultured islets were centrifuged at 1400 rpm for 1 minute and washed with Ca-free Kerbs-Henseleit (KH) buffer (4.7 mM KCl, 25 mM HEPES, 1.2 mM $KH_2PO_4$, 1.2 mM $MgSO_4 \times 7H_2O$, 135 mM NaCl, pH≈7.4, osmotic pressure≈290 mOsm). After the wash, the islets were centrifuged again and all supernatant was aspirated. Then, the collected islets were encapsulated following the protocol mentioned above. As the islets had variable sizes (50-400 μm), the total number of encapsulated islets were converted into islet equivalences (IE, normalized to 150 μm size) based on a previously published method (Ricordi et al., "Islet Isolation Assessment in Man and Large Animals," *Acta Diabetol. Lat.* 27:185-195 (1990), which is hereby incorporated by reference in its entirety).

Implantation/Transplantation Surgeries. Immune-competent male C57BL/6 mice were utilized for transplantation. To create insulin-dependent diabetic mice, healthy C57BL/6 mice were treated (50 mg/kg mouse) with freshly prepared Streptozocin (STZ) (Sigma-Aldrich) solution (7.5 mg/mL in sodium citrate buffer solution) for 5 consecutive days. The blood glucose levels of all mice were retested prior to transplantation. Only mice whose non-fasted blood glucose levels were above 300 mg/dL were considered diabetic and underwent transplantation. The non-diabetic or STZ-induced diabetic mice were anesthetized with 3% isoflurane in oxygen. The abdomen of each mouse was shaved and sterilized using betadine and 70% ethanol. Preoperatively, all mice received 0.3 mL of 0.9% saline subcutaneously to prevent dehydration. A ~1 mm incision was made along the midline of the abdomen and the peritoneal lining was exposed using blunt dissection. The peritoneal wall was then grasped with forceps and a ~1 mm incision was made along the linea alba. The device was then inserted into the peritoneal cavity through the incision. The incision was closed using 5-0 taper tipped polydioxanone (PDS II) absorbable sutures. The skin was then closed over the incision using a wound clip.

Dog Laparoscopic Procedure. Dogs were premedicated with glycopyrrolate and butorphanol, induced with propofol, and anesthetized with isoflurane. The abdomen was clipped and prepared for sterile surgery. A 10 mm laparoscopic port was inserted into the abdomen on midline 1 cm caudal to the umbilicus using the Hasson technique. The abdomen was insufflated to 12 mm Hg pressure with $CO_2$. A 5 mm laparoscopic port was percutaneously inserted into the left abdomen at a point 3 cm lateral and 2 cm cranial to the umbilicus. A second 5 mm laparoscopic port was placed in the right side of the abdomen at a point 3 cm lateral and 2 cm cranial to the umbilicus. A 10 mm rigid endoscope was introduced through the 10 mm port to enable visualization of the abdomen. A TRAFFIC system was inserted into the abdomen through the left side laparoscopic port. A laparoscopic probe was introduced through the right sided 5 mm port and was used to manipulate the TRAFFIC system so that it was either placed between the liver and the diaphragm or disbursed in the cranial abdomen. In cases in which the device was disbursed throughout the cranial abdomen, the top of the device was secured to the abdominal wall using 3-0 polydioxanone suture material placed through the head of the TRAFFIC system and the edge of the left side 5 mm port site. The remaining ports were then removed and the port sites were closed with 3-0 polydioxanone suture material.

Blood Glucose Monitoring (Mice). Blood glucose levels were monitored three times a week following the transplant surgery in the mice. A small drop of blood was collected from the tail vein using a lancet and tested using a commercial glucometer (Clarity One, Clarity Diagnostic Test Group, Boca Raton, FL). Mice with unfasted blood glucose levels below 200 mg/dL were considered normoglycemic.

Retrieval of Materials (Mice). At desired time points post-implantation or transplantation (with encapsulated cells), the mice were anesthetized using 3% isoflurane in oxygen and maintained at the same rate throughout the procedure. Preoperatively, all mice received 0.3 mL of 0.9% saline subcutaneously to prevent dehydration. The abdomen of the mice were shaved and alternately scrubbed with betadine and 70% ethanol to create a sterile field before being transferred to the surgical area. A ~5 mm incision was made along the midline of the abdomen and the peritoneum was exposed using blunt dissection. A ~5 mm incision was made on the peritoneum and the device was grasped and pulled out by using blunt forceps. The incision was closed with 5-0 taper tipped polydioxanone (PDS II) absorbable suture and the skin was closed over the incision using wound clips.

Retrieval of Materials (Dogs). Dogs were premedicated with glycopyrrolate and butorphanol, induced with propofol, and anesthetized with isoflurane. The abdomen was clipped and prepared for sterile surgery. A 10 mm laparoscopic port was inserted into the abdomen on midline 1 cm caudal to the umbilicus using the Hasson technique. The abdomen was insufflated to 12 mm Hg pressure with $CO_2$. A 5 mm laparoscopic port was percutaneously inserted into the left abdomen at a point 3 cm lateral and 4 cm cranial to the umbilicus. A second 5 mm laparoscopic port was placed in the right side of the abdomen at a point 3 cm lateral and 4 cm cranial to the umbilicus. A 10 mm rigid endoscope was introduced through the 10 mm port to enable visualization of the abdomen. The previously inserted TRAFFIC system was located and photographed. The TRAFFIC system was grasped with laparoscopic Kelly forceps and dissected from attached omentum if necessary. The TRAFFIC system was then removed from the abdomen through the left side 5 mm port site. In those cases in which the device was previously secured to the abdominal wall, a 1 cm full thickness circle of full-thickness body wall with the suture fixation at the center was resected. The remaining ports were removed and the dogs were humanely euthanatized.

Histological Analysis. The retrieved devices were fixed in 4% paraformaldehyde, embedded in paraffin, and sectioned by the Cornell Histology Core Facility. Ten-micrometer-thick paraffin sections were stained with hematoxylin/eosin. For staining of insulin with immunofluorescence, paraffin-embedded sections were rehydrated by sequentially washing in xylene, 100%, 95%, 75% ethanol, and water. Then slides were boiled in 1 mM EDTA for antigen exposure. After blocking, primary Guinea pig anti-rat insulin antibody (Linco, 1:200) were applied and incubated overnight at 4° C., followed with wash and incubation with FITC-conjugated Donkey anti-Guinea pig IgG (Jackson Immunoresearch, 1:200). Slides were washed twice with water, applied with antifade/DAPI, and covered with coverslips. Fluorescence images were captured under a ZeissLSM710 confocal microscope at Cornell Biotechnology Resource Center Imaging Facility.

Results

Figure 2B:
FIG. 2B is a schematic illustration showing the fabrication steps of the implantable therapeutic delivery system of FIG. 2A.
Figures 2C, 2D, 2E, 2F:
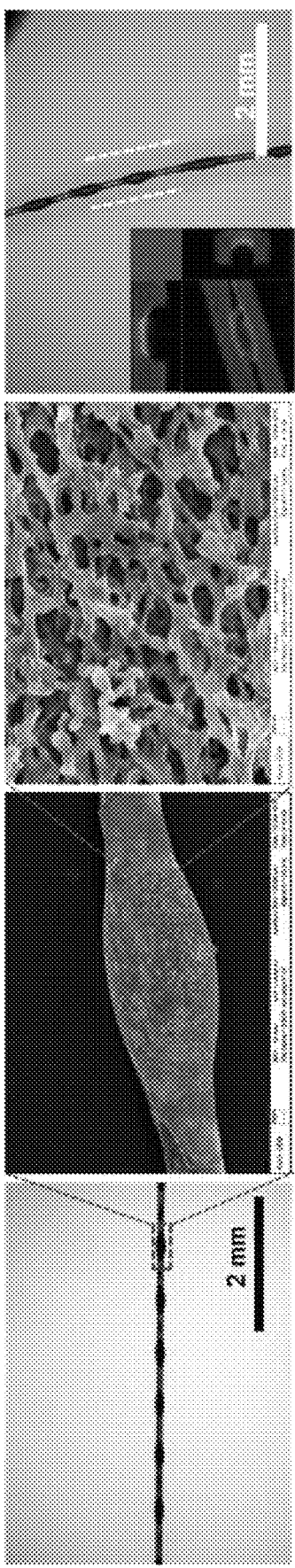
FIGS. 2C-E are digital images showing morphology characterizations of the beads-on-strand implantable therapeutic delivery system.
FIG. 2F is an optical microscope image of the implantable therapeutic delivery system without cell loading, with the inset being a confocal microscope image of the implantable therapeutic delivery system.
Figure 2G:
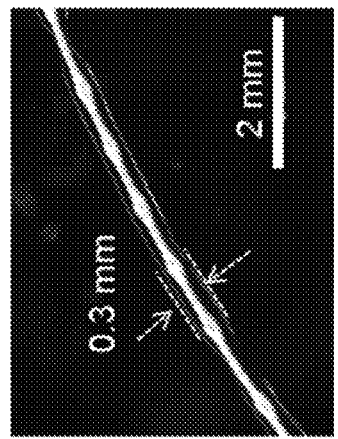
FIGS. 2G-J illustrate the hydrogel layer diameter control data.
Figure 2H:
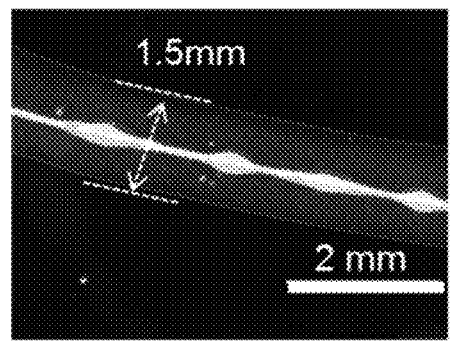
Figure 2I:
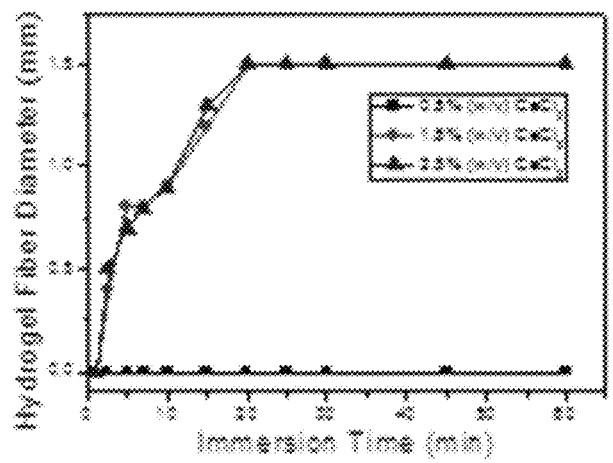
Figure 2J:
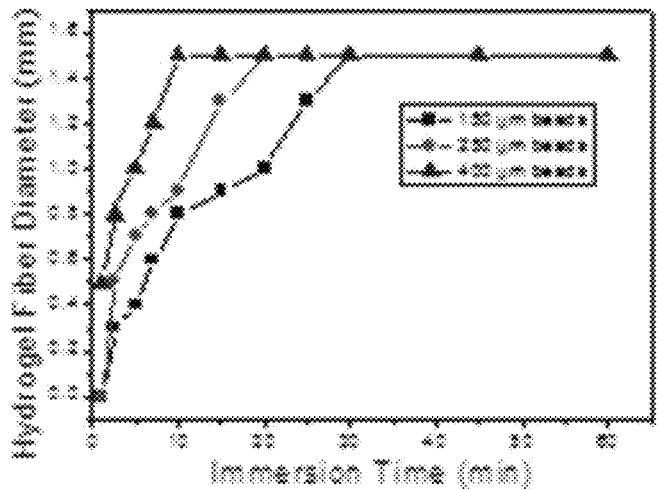

To fabricate the TRAFFIC system having the structure shown in FIG. 2A, a strand with a periodic array of hydrophilic, porous $Ca^{2+}$-releasing beads was first made (Steps 1-2 in FIG. 2B) and then the modified strand was submerged in an alginate solution to form a fiber (Step 3 in FIG. 2B). The bead-decorated strand was fabricated using a modification of a method described in an earlier publication (Zheng et al., "Directional Water Collection on Wetted Spider Silk," *Nature* 463:640-643 (2010), which is hereby incorporated by reference in its entirety). Briefly, a 70 μm nylon strand was dip-coated horizontally with a viscous 7% (weight/volume) poly(methyl methacrylate) (PMMA) solution that was dissolved in N,N-dimethyl formamide (DMF) and contained 2.5% $CaCl_2$. The coating solution formed a thin film on the nylon strand and spontaneously broke up into a regular array of droplets on the strand due to the surface tension driven Rayleigh instability (Quere et al., "Wetting of Fibers—Theory and Experiments," *Rev. Phys. Appl.* 23:1023-1030 (1988), which is hereby incorporated by reference in its entirety). After the drying, a "beads-on-a-strand" structure was formed (FIGS. 2C-D). The beads had an oval shape, slightly elongated along the strand axis with a transverse diameter of about 150 μm. Interestingly, the beads were highly porous as shown by the sponge-like structures in FIG. 2E. The formation of pores on the beads is believed to be due to the drying process and improves the adhesion between the beads and the subsequently formed hydrogel fiber.

The modified strand was then immersed in a 2% alginate solution for 4 minutes and a hydrogel fiber with a diameter of about 700 μm was formed around the strand in situ. The strand-reinforced hydrogel fiber was further cross-linked by transferring it to a 20 mM $BaCl_2$ solution for another 5 minutes. FIG. 2F shows a representative image of the final hydrogel fiber. Unlike the hydrogel fibers reported previously using microfluidic techniques where the alginate was crosslinked from an external source, the hydrogel fiber described here was formed through an internal crosslinking by the calcium released from the strand. The porous beads provided increased surface areas for the calcium release. This approach ensured the relatively uniform thickness of alginate hydrogel around the strand. The confocal fluorescent images (FIG. 2F, inset) confirmed the concentric structure of the composite fiber where the anchoring beads were labeled with a Rhodamine (red) fluorescent dye and the alginate was chemically conjugated with an Alexa Fluor (green) dye.

Next, it was demonstrated that the diameter of the hydrogel fiber could be easily controlled between 300 μm to 1.5 mm by adjusting different parameters (FIGS. 2G-J). For example, higher $Ca^{2+}$ content in the coating solution led to a larger diameter hydrogel fiber given the same immersion time. Larger diameter beads made by repeated dip-coatings also increased the fiber size. Given the same beaded-string, the fiber size could also be controlled by adjusting the immersion time. Interestingly, when the $Ca^{2+}$ content in the coating solution was too low (<0.5%), no hydrogel fiber formed regardless of immersion time. This was probably because the amount of $Ca^{2+}$ released was not sufficient to crosslink the alginate. It was also interesting that the hydrogel fiber size saturated over time at 1.5 mm.

Figure 22A:
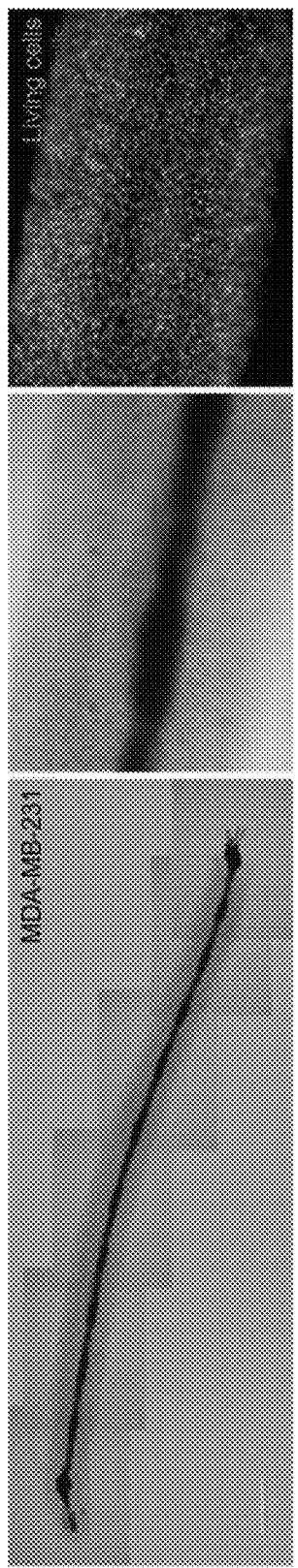
FIGS. 22A-C show live/dead staining of cells after overnight culture post-encapsulation, including MDA-MB-231 mammary cancer cells (FIG. 22A), human embryonic stem cell (hESCs) derived pancreatic progenitors (PPs) (FIG. 22B), and human hepatocyte-stromal cell aggregates (FIG. 22C).
Figure 22B:
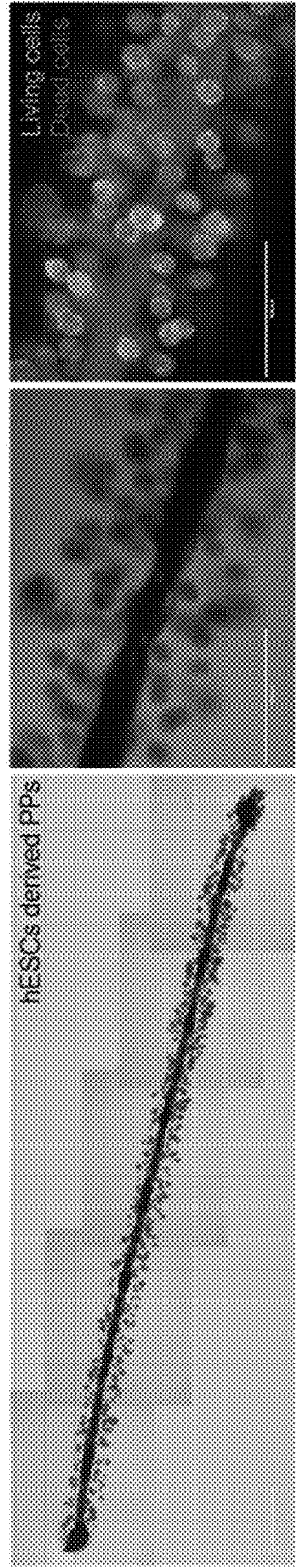
Figure 22C:
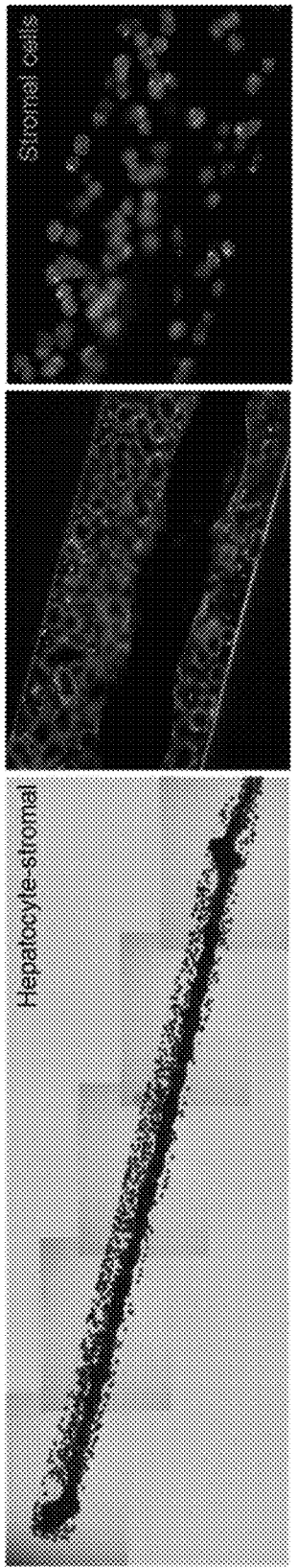
Figure 23A:
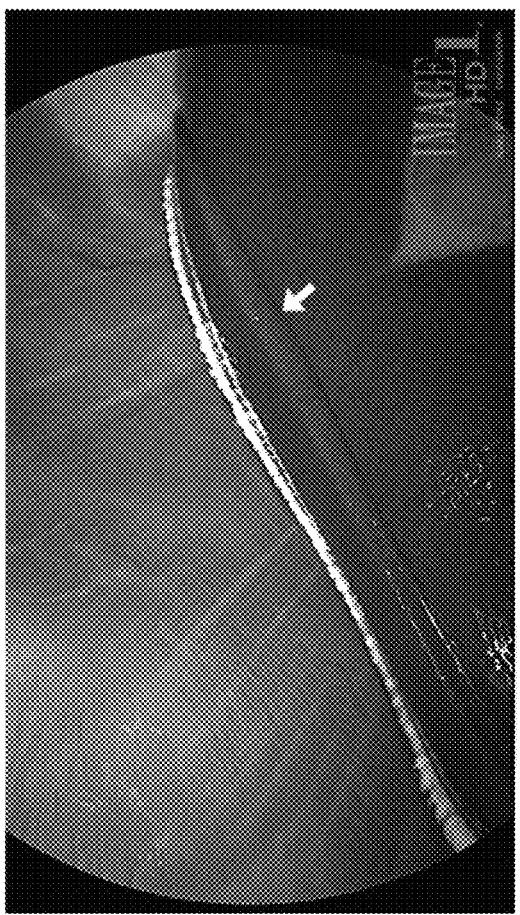
FIGS. 23A-D are images relating to the TRAFFIC system described herein which, when placed cranial to the liver in a dog, the TRAFFIC system made an indentation on the liver. Liver parenchyma deep to the indentation was completely normal, suggesting that the TRAFFIC system was bio-inert.
Figure 23B:
Figure 23C:
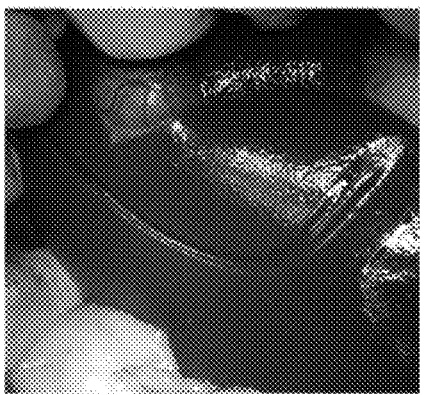
Figure 23D:
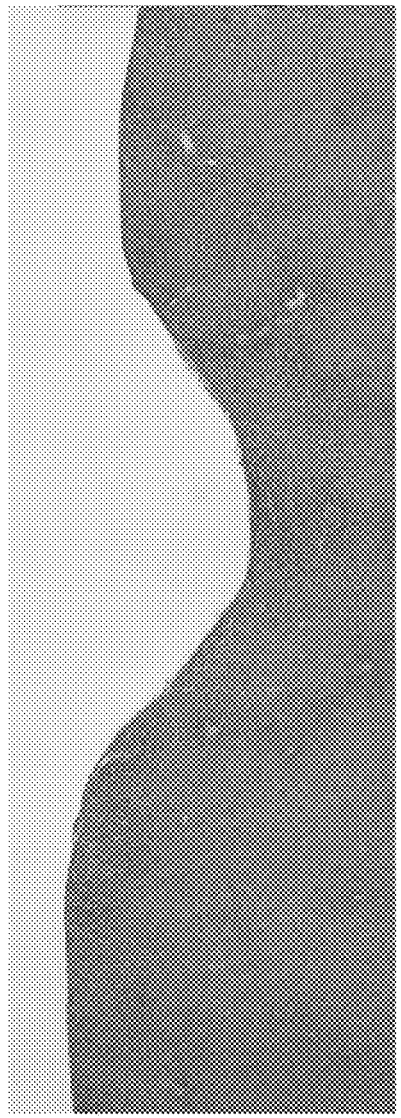

The ability to control the strand size made it possible to engineer hydrogel fibers to meet different specific requirements. Smaller diameter fibers have higher surface area for mass transfer while larger diameter fibers have higher capacity for islet encapsulation. The diameter of the fibers may also affect biocompatibility (discussed infra). Moreover, it was very simple to incorporate therapeutic cells into the TRAFFIC system by dispersing cells in the alginate solution at a pre-determined cell density. As shown in FIG. 2K, rat pancreatic islets were isolated and successfully encapsulated into the TRAFFIC system. After overnight culture post-encapsulation, live/dead staining of the islets showed excellent viability of the cells (FIG. 2L). In addition, it was further demonstrated that this platform can also be applied to other types of cells, such as model cells, MDA-MB-231 mammary cancer cells (FIG. 22A), human embryonic stem cell (hESCs) derived pancreatic progenitors (PPs) (FIG. 22B) and human hepatocyte-stromal cell aggregates (FIG. 22C). The viability and functionality of these cells were tested and discussed infra.

Figure 8A:
FIG. 8A is a digital image showing EDS element mapping of a beads-on-strand embodiment of an implantable therapeutic delivery system.

EDS element mapping was conducted by using a scanning electron microscope to check the calcium distribution in this TRAFFIC system. As shown in FIG. 8A, the calcium chloride was uniformly distributed along the whole beaded string structure. The EDX spectrum showed identical peaks of calcium and chloride (FIG. 8B), suggesting the existence of calcium chloride on the entire surface.

Previous studies have demonstrated that the geometry of implanted biomedical devices can modulate foreign body response and fibrosis (Kusaka et al., "Effect of Silica Particle Size on Macrophage Inflammatory Responses," *PLoS ONE* 9:e92634 (2014); Zandstra et al., "Microsphere Size Influences the Foreign Body Reaction," *Eur. Cells Mater.* 28:335-347 (2014); Matlaga et al., "Tissue Response to Implanted Polymers: The Significance of Sample Shape," *J. Biomed. Mater. Res.* 10:391-397 (1976); and Salthouse, "Some Aspects of Macrophage Behavior at the Implant Interface," *J. Biomed. Mater. Res.* 18:395-401 (1984), which are hereby incorporated by reference in their entirety). Circular rods produced less fibrosis than pentagonal or triangular rods (Matlaga et al., "Tissue Response to Implanted Polymers: The Significance of Sample Shape," *J. Biomed. Mater. Res.* 10:391-397 (1976), which is hereby incorporated by reference in its entirety). In addition, a recent study showed that the size of the spherical alginate hydrogel beads plays an important role in induction/prevention of fibrosis (Veiseh et al., "Size- and Shape-Dependent Foreign Body Immune Response to Materials Implanted in Rodents and Non-Human Primates," *Nature Mat.* 14:643-651 (2015), which is hereby incorporated by reference in its entirety). The thickness of the alginate layer in the TRAFFIC system was varied and the foreign body response was tested by implanting the devices into the intraperitoneal (IP) space of C57BL/6 mice. The C57BL/6 mouse strain has been known to produce more severe fibrosis than other strains, such as the Balb/c mice or Lewis rats (King et al., "The Effect of Host Factors and Capsule Composition on the Cellular Overgrowth on Implanted Alginate Capsules," *J. Biomed. Mater. Res.* 57:374-383 (2001), which is hereby incorporated by reference in its entirety).

A 2-week study was first conducted, because it was reported that obvious fibrosis appeared within 2 weeks of implantation in the IP space with other implants (Veiseh et al., "Size- and Shape-Dependent Foreign Body Immune Response to Materials Implanted in Rodents and Non-Human Primates," *Nature Mat.* 14:643-651 (2015), which is hereby incorporated by reference in its entirety). In this study, two different size implants were tested. In the "big" group (n=5) mice were implanted with TRAFFIC systems having ~1.5 mm diameter, and in the "small" group (n=5) mice implanted with TRAFFIC systems of ~400 μm diameter. A single 2.5 cm long "big" or "small" device was implanted into the IP space of each mouse. FIGS. 3A and 3E are microscopic images of the "big" (FIG. 3A) and "small" (FIG. 3E) devices at the time of implant. After 2 weeks, the devices were retrieved and characterized. Optical microscopy was used to evaluate cellular overgrowth on the devices. It was found that there were many more cells attached to the 400 μm (FIGS. 3F-H) diameter devices than the 1.5 mm diameter devices (FIGS. 3B-D). H&E staining showed that there were almost no cells attached to the 1.5 mm TRAFFIC system (FIG. 3C), while the smaller diameter devices were enveloped with multiple layers of fibrotic tissue (FIG. 3G). Cellular deposition was further examined using Z-stacked confocal imaging using DAPI (nucleus marker), F-actin (cellular cytoskeleton marker), and alpha-smooth muscle actin (α-SMA, myofibroblast marker). These data all showed that the larger diameter devices had significantly reduced fibrotic deposition (compare FIG. 3D and 3H). A long-term study (90 days) was then conducted to consolidate the results and to evaluate the possibility that the different fibrotic response was due to inadequate time for cells to cover the larger diameter device. Dark field phase contrast images from retrieved devices showed a marked reduction in cellular deposition on the larger diameter devices (FIG. 3J) compared to smaller diameter devices (FIG. 3N). Histologic and immunohistochemistry analysis also confirmed this tendency (compare FIGS. 3K-L to FIGS. 3O-P).

To further demonstrate the stability of the TRAFFIC system and the possibility of implanting/retrieving a scaled-up TRAFFIC system in a larger animal model, the device was implanted into a dog model by using a minimally invasive laparoscopic procedure. As shown in FIGS. 4A-I, a TRAFFIC system of ~20 cm in length was implanted intraperitoneally into 4 dogs using laparoscopy. The device was placed between the liver and diaphragm (FIG. 4A). After 2 weeks, another laparoscopic procedure was done to retrieve the device. As shown in FIG. 4D, the TRAFFIC system remained between the liver and the diaphragm, and there was no observable tissue adherence or fibrosis generated based on microscopic examination (FIG. 4E) and histologic analysis (FIG. 4F) (compare to microscopic examination (FIG. 4B) and histologic analysis (FIG. 4C) of implant at day 0). There was no cell attachment to the device (FIGS. 4B-C). This result suggests that the TRAFFIC system is minimally reactive in a large animal model and may be an ideal translational cell encapsulation device.

Figure 8B:
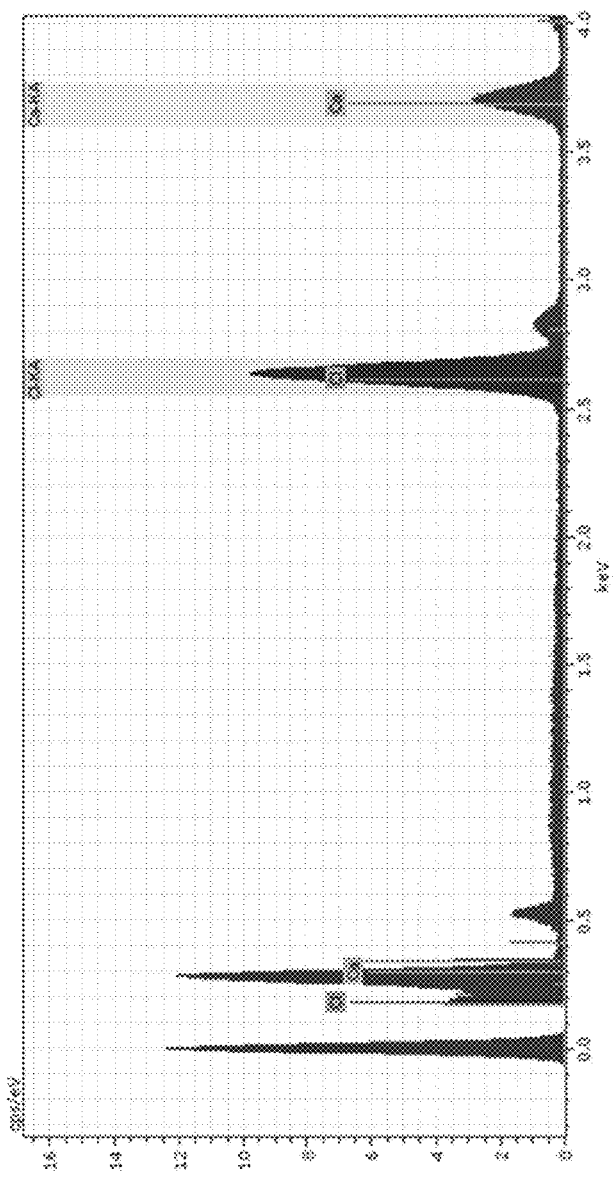
FIG. 8B is an EDX spectrum of a bead surface from the implantable therapeutic delivery system of FIG. 8A.

Even though the TRAFFIC system implanted in one dog caused no foreign body response, an issue of implant strength was identified in this experiment. As shown in FIGS. 4G-I, there was a break on the hydrogel layer in 3 dogs. This damage of the hydrogel layer could have been caused by the movement of the dog or during implantation. This implied that the mechanical strength, especially the attachment between the hydrogel layer and the reinforcement layer, needed to be improved. Thus, the calcium element distribution along the suture was analyzed by doing EDS element mapping. As shown in FIGS. 8A-B the calcium and chlorine elements were periodically distributed along the fiber, co-located with the anchoring beads. It indicated that the alginate hydrogel was crosslinked more firmly around the anchoring beads than the bare suture parts, and this lack of uniformity may have caused a focally weak hydrogel attachment.

Figure 5A:
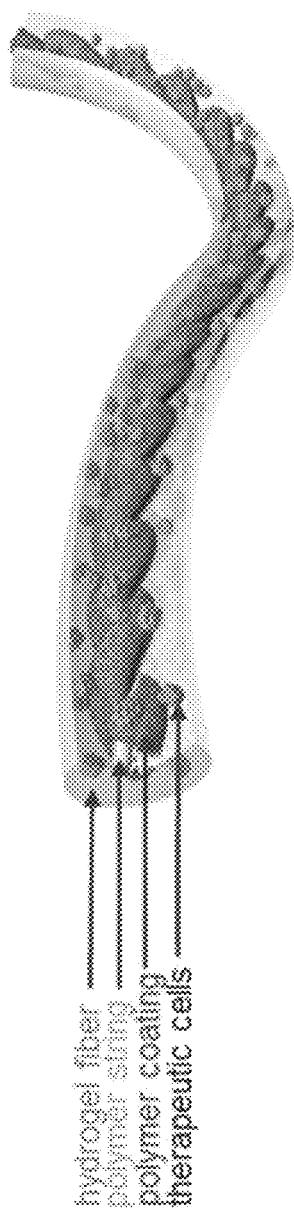
Figure 5B:
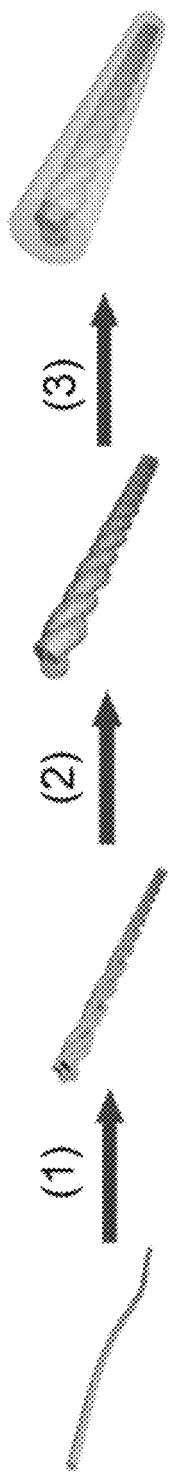
FIG. 5B is a schematic illustration of the fabrication steps of the implantable therapeutic delivery system shown in FIG. 5A.

Therefore, to improve the mechanical stability of the TRAFFIC system, a system based on "twisted sutures" design was developed (FIG. 5A). To fabricate this new TRAFFIC system, as shown in FIG. 5B, two sutures were first twisted together, then the torsion was released by self-twisting from the middle of the double helical structure to form a stable helical structure with four strands twisted together. The twisted sutures were then dipped in PMMA:CaCl$_2$/DMF solution to be modified with a layer of polymer coating. The modified twisted sutures were dipped in alginate solution to crosslink a uniform layer of alginate hydrogel in situ. Compared to a single strand of suture with smooth surface, the twisted sutures had many continuous longitudinal grooves. These structures contributed to the wettability, so that the polymer solution could easily wet the whole structure without forming beads. Detailed theoretical explanation is discussed infra. The surface modification process was tracked by digital imaging (FIGS. 5C-E) and fluorescent imaging (FIGS. 5I-K). Scanning electron microscopy (SEM) was used to examine the micro-nano structures of the device. FIG. 5F is an SEM image showing a typical helical twisted suture structure with four strands. FIGS. 5G-H are SEM images of the polymer modified twisted sutures, which indicate the uniform coating of the polymer layer and the porous surface of the polymer layer. Fluorescent microscope images (FIGS. 5I-K) also confirm the uniform coating of both the polymer layer (FIG. 5J) and the alginate hydrogel layer (FIG. 5K). In addition, EDS element mapping was conducted by using a scanning electron microscope again to check the calcium distribution in this new TRAFFIC system design. As shown in FIGS. 5L-N, the calcium chloride was uniformly distributed along the whole twisted sutures structure. The EDX spectrum showed identical peaks of calcium and chloride (FIG. 5O), suggesting the existence of calcium chloride on the entire surface. The capability of cell encapsulation application was demonstrated in vitro by encapsulating hESCs-derived pancreatic progenitor aggregates (PPs) in this new TRAFFIC system (FIGS. 5P-Q). The TRAFFIC system containing PPs was cultured in medium for 3 days and stained with live/dead staining assay. As shown in FIG. 5R, most of the encapsulated cells were still alive, indicating biocompatibility of the new TRAFFIC system.

Figure 9A:
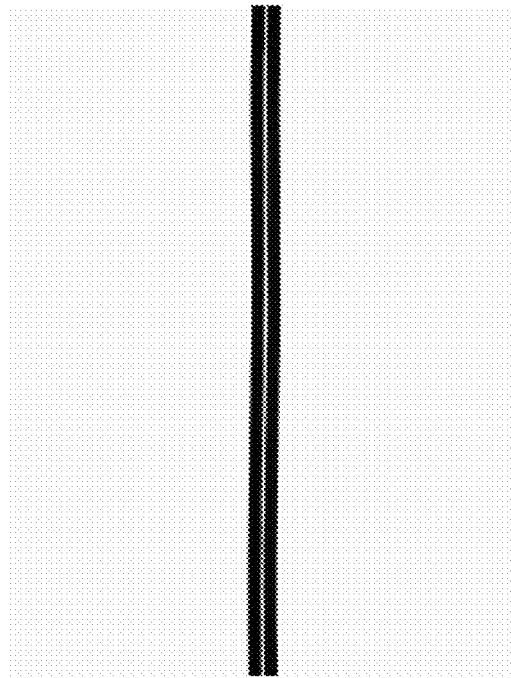
FIGS. 9A-D are goniometer images of a PMMA:CaCl$_2$/DMF solution wetted single strand nylon suture (FIGS. 9A-B) and twisted sutures (FIGS. 9C-D).
Figure 9B:
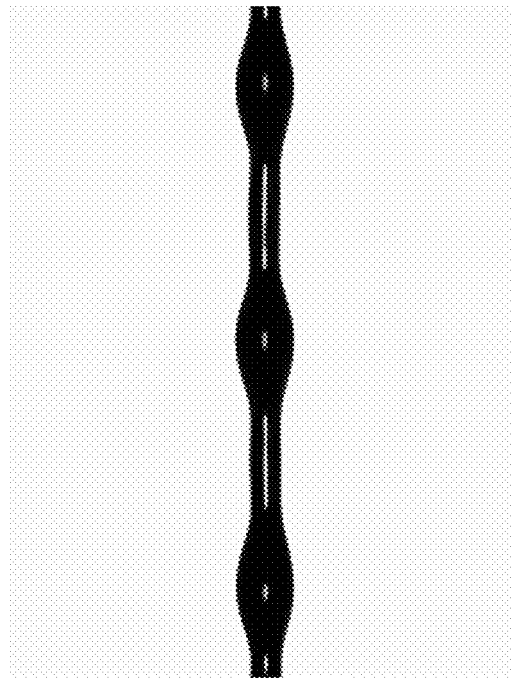
Figure 9C:
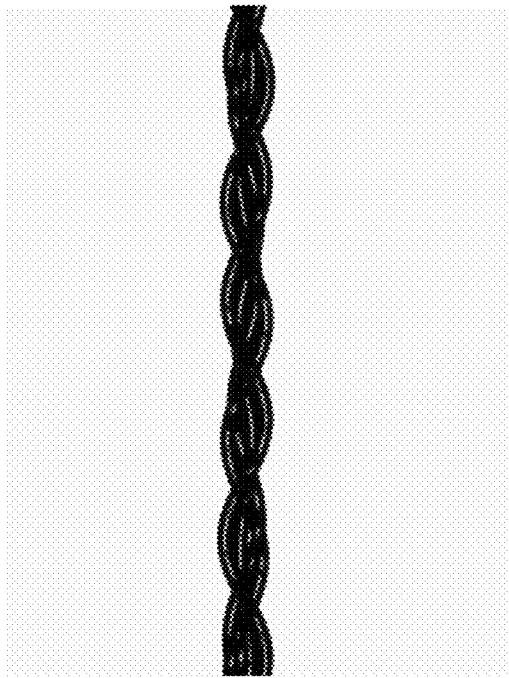
Figure 9D:
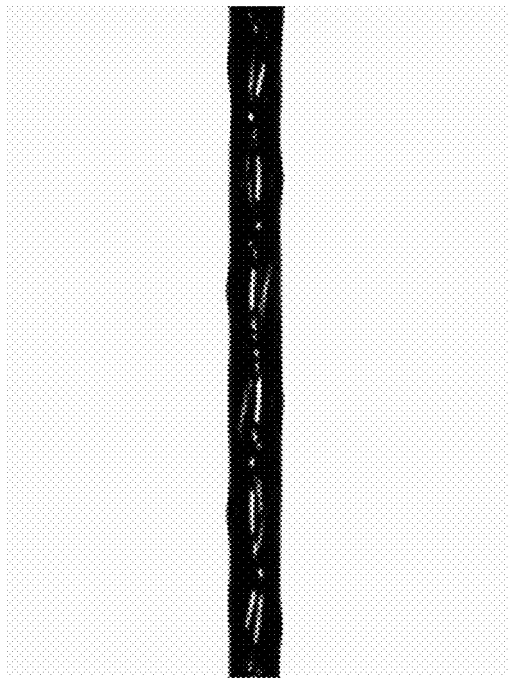

FIGS. 9A-9D are images showing the impact of string structure to polymer coating geometry. FIGS. 9A-9B show a single straight strand (FIG. 9A) and the formation of polymer beads on the single straight strand (FIG. 9B). In contrast, the twisted strand in FIG. 9C, when coated with a polymer coating (FIG. 9D), does not form a beaded geometry.

Figure 6H:
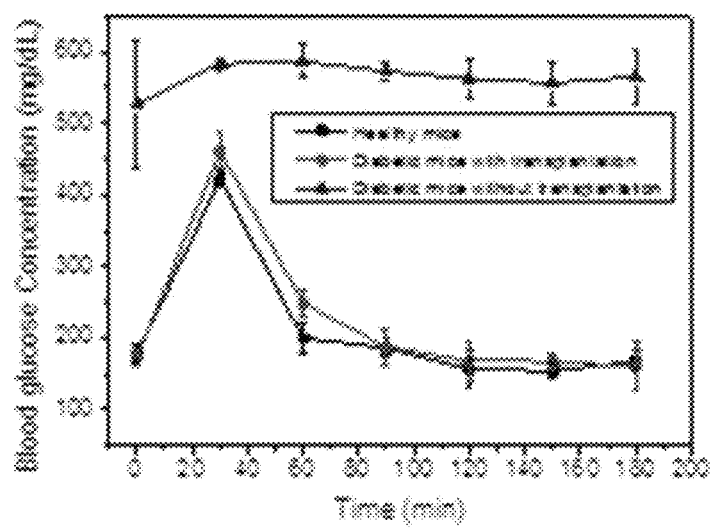

To explore the therapeutic potential of the TRAFFIC system, the encapsulated rat islets were transplanted into chemically induced C57BL/6 diabetic mice (FIG. 6A). C57BL/6 mice were chosen because this strain was known to produce a strong fibrotic response against the alginate capsules, higher than other mouse strains such as the Balb/c mice or Lewis rats. Firstly, rat pancreatic islets were isolated according to a previous reported protocol (Lacy and Kostianovsky, "Method for the Isolation of Intact Islets of Langerhans from the Rat Pancreas," *Diabetes* 16:35 (1967), which is hereby incorporated by reference in its entirety) (FIG. 6B). Then the isolated rat islets were encapsulated into the TRAFFIC system at a density of about 20 islets equivalencies (IE's) per mm TRAFFIC system in length (FIG. 6C). Each STZ-induced diabetic mouse received a transplant of a TRAFFIC system containing rat islets of about 1 inch or approximately 500 IE's through an intraperitoneal implantation. FIG. 6G shows the blood glucose concentration ("BG") over time post-transplantation. The diabetes was reversed 2 days after the implantation and remained cured (i.e., BG<200 mg/dL) for at least 4 weeks when the experiment was ended. At day 28 after transplantation, an intraperitoneal glucose tolerance test (IPGTT) was conducted. As shown in FIG. 6H, the BG boosted up above 400 mg/dL in both healthy and diabetic mice after IP injection of glucose. Then the BG gradually decreased back to the normal range after 90 min, indicating that the transplanted islets were still functional. The devices were retrieved and all the mice returned to a diabetic state, confirming the effectiveness of a TRAFFIC system containing rat islets in regulating the blood glucose level and controlling diabetes. The retrieved devices had no visible tissue adhesion or extensive fibrosis (FIG. 6D). Histological studies (FIGS. 6E-F) revealed only a very thin (about 1-2 layers of cells) layer of cellular overgrowth. The encapsulated islets appeared normal, which is in correspondence with the BG and IPGTT data. These islet encapsulation and diabetic model experiments were repeated 3 times.

Figure 7A:
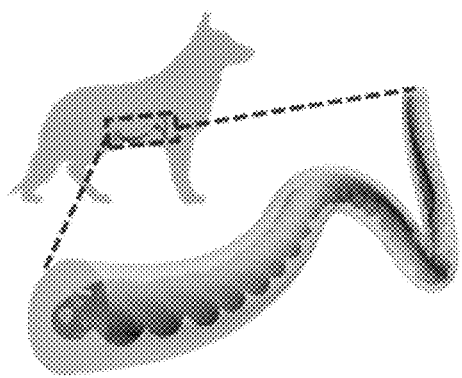
Figure 7G:
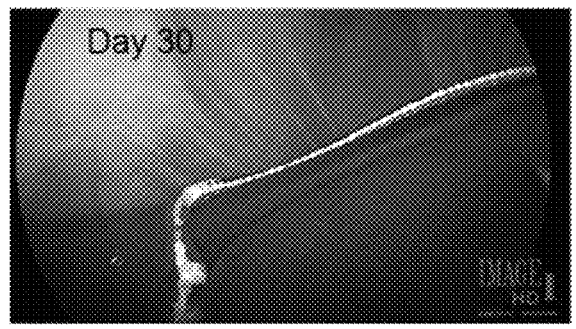
Figure 7H:
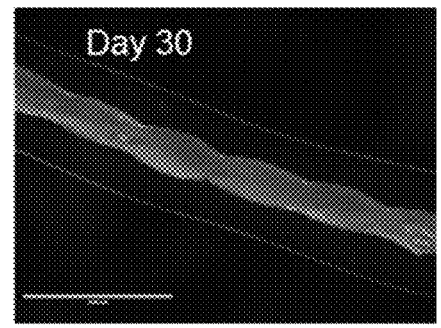
Figure 7I:
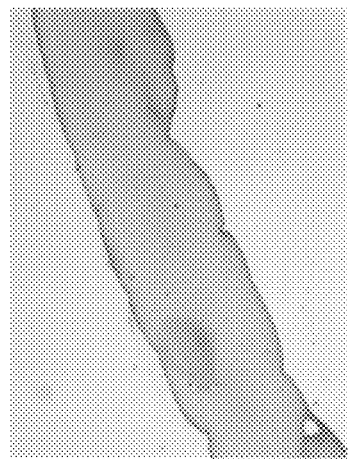
Figure 7J:
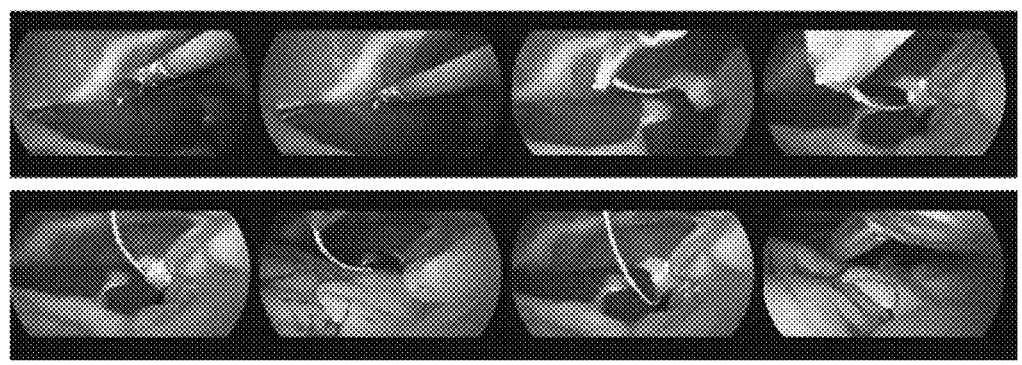
Figure 10A:
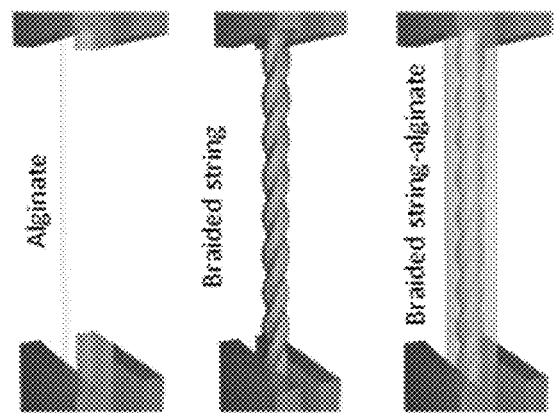
FIGS. 10A-C relate to a mechanical stability test of one embodiment of an implantable therapeutic delivery system.
Figure 10B:
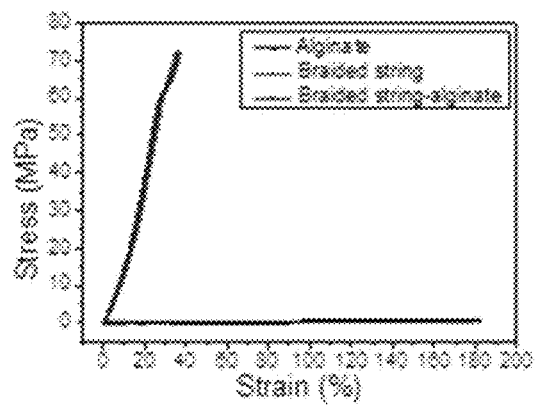
Figure 10C:
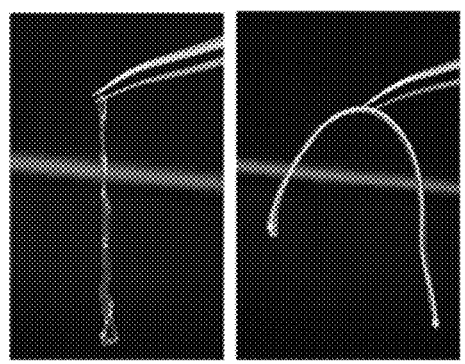

As mentioned above, by changing to the "twisted strand" design, the mechanical stability of the TRAFFIC system was greatly improved (FIGS. 10A-10C). Therefore, another experiment was conducted to confirm the feasibility of implantation/retrieval in a dog model and to test the stability of the new version of the TRAFFIC system (FIG. 7A). A TRAFFIC system based on the "twisted strand" design of about 30 cm in length and 1.5 mm in diameter was fabricated. The device was loaded into a 1 mL pipette and inserted into the IP space through a 5 mm laparoscopic trocar (FIG. 7B). The TRAFFIC system was manipulated laparoscopically and as shown in FIG. 7E, the TRAFFIC system was inserted between the liver and diaphragm to avoid the reach of the omentum. After one month, another laparoscopic surgery was conducted to retrieve the device. As shown in FIG. 7G, the TRAFFIC system was still in place cranial to the liver and there was no tissue adhesion at all. More interestingly, the TRAFFIC system made an indentation on the liver. Histological studies (FIGS. 23A-D) that liver parenchyma deep to the indentation was completely normal, suggesting that the TRAFFIC was bio-inert. The TRAFFIC system was easily retrieved laparoscopically (FIG. 7J), and then examined microscopically. As shown in FIG. 7H, the TRAFFIC system surface was intact with no cell attachment seen. There was no obvious change in shape of the device compared to pre-implantation (compare FIGS. 7H and 7F), suggesting that the helical TRAFFIC system configuration has improved durability compared to the original design. Histological analysis shown in FIG. 7I further demonstrated that there was no cell attachment on the device.

Discussion

The therapeutic potential of cell encapsulation was demonstrated nearly 40 years ago and a tremendous amount of work has been done since that time. Yet, the geometrical formats of encapsulating materials most commonly used today have remained largely the same (Raof et al., "One-Dimensional Self-Assembly of Mouse Embryonic Stem Cells Using an Array of Hydrogel Microstrands," *Biomaterials* 32:4498-4505 (2011)): cylindrical (such as hollow fibers), planar (such as hydrogel sheets), or spherical (microcapsules). While great progress has been made in each category, especially for islets encapsulation for T1D treatment, critical challenges remain. The TRAFFIC system design is radically different and can fundamentally transform the entire cell encapsulation field.

Compared with current macroscopic devices, either tubular or planar, the TRAFFIC system has a biocompatible hydrogel exterior and a large surface area for mass transfer. It is mechanically robust and has no sealing or leaking problems (Writing Team for the Diabetes Complications Trial/Epidemiology of Diabetes & Complications Research, "Sustained Effect of Intensive Treatment of Type 1 Diabetes Mellitus on Development and Progression of Diabetic Nephropathy: The Epidemiology of Diabetes Interventions and Complications (EDIC) Study," *JAMA* 290:2159-2167 (2003)). Compared with current hydrogel microcapsules, the thin, flexible "twisted sutures" allow easier handling and manipulation. It makes cell encapsulation much easier and more accessible. No microfabrication or droplet generators are needed. The "twisted sutures" can be used as an off-the-shelf, ready-for-use platform for researchers and clinicians. In addition, it is possible to control how close to the surface implanted cells are located (the diffusion distance) by adjusting the diameters of the string and the hydrogel fiber around it. The short diffusion distance is beneficial for not only cell survival but also for rapid glucose responsiveness (Weir et al., "Scientific and Political Impediments to Successful Islet Transplantation," *Diabetes* 46:1247-1256 (1997); Dufrane et al., "Macro- or Microencapsulation of Pig Islets to Cure Type 1 Diabetes," *World J. Gastroenterol.* 18:6885-6893 (2012), which are hereby incorporated by reference in their entirety). The polymer coating may be made of a slowly biodegradable polymer (e.g., polycaprolactone) containing anti-inflammatory drugs (e.g., dexamethasone) to mitigate the foreign body response.

Most importantly, the TRAFFIC system design enables convenient retrieval and replacement. Traditional methods to retrieve microcapsules using peritoneal lavage are invasive and time-consuming, and it is almost impossible to retrieve all the microcapsules given the complex structures of different organs in the peritoneal cavity. Even with repeated, invasive peritoneal lavages, up to 40% microcapsules may not be retrieved in mice (Lee et al., "Synthesis of Cell-Laden Alginate Hollow Fibers Using Microfluidic Chips and Microvascularized Tissue-Engineering Applications," *Small* 5:1264-1268 (2009)). The retention percentage could be similar or even higher in humans where 1,000 times more microcapsules are typically transplanted. With a minimally invasive laparoscopic surgery, the TRAFFIC system can be easily and completely retrieved. For any transplantation, straightforward removal after completion of therapy or failure of transplant will address patients' concerns of having foreign materials and cells permanently implanted in their body. It will also allow researchers and physicians the ability to study the mechanism for any implant failure by examining the retrieved implant in its entirety. As therapeutic cells derived from stem cells or adult cells become a potential alternative to primary cells, the retrievability and mechanical robustness of the device is more highly desired to mitigate the concerns of teratoma formation. Lastly, different hydrogel-forming materials including those that do not easily form spherical capsules using droplet generators can also be used. This platform technology will critically transform the way therapeutic cells are encapsulated and delivered.

Example 2—Comparison of the Fiber-Hydrogel Frictions Between Beads-on-Strand Design and Twisted Strand Design Mechanical robustness is one of the most significant properties of an implantable/retrievable biomedical device. During the development of the beads-on-Strand ("BOS") design devices (described supra), it was found that occasionally the alginate hydrogel layer would detach from the inner reinforcement, especially along the long axis of the fiber. It was also found that the inner strand could be rather easily pulled out of the hydrogel shell. However, when changed to the twisted strand design, it was found that it was much more difficult to pull out the reinforcement strand. To investigate this relationship further, the frictional forces between the hydrogel layer and the reinforcement strands was analyzed.

Figure 11B:
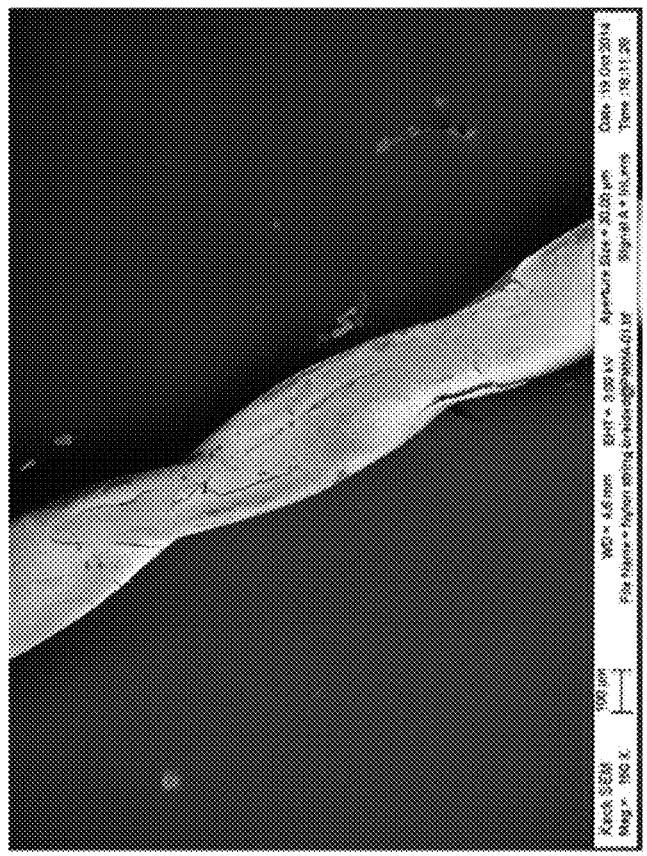
FIGS. 11A-B are SEM images of the reinforcement strands of two different embodiments of an implantable therapeutic delivery system.
Figure 11A:
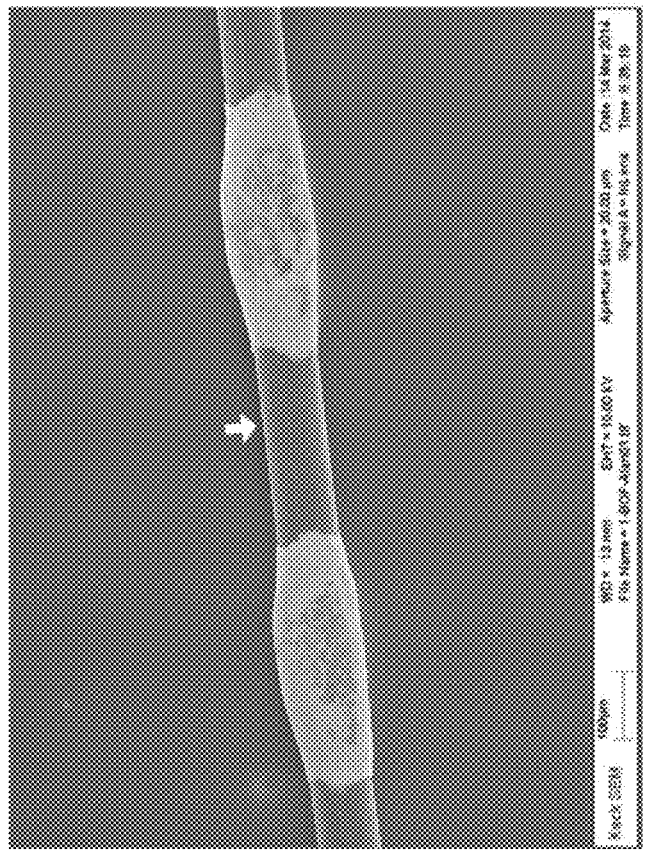

When the SEM images of the two reinforcement strands were compared, it was noticed that in the BOS design there were regions of bare suture between the beads (FIG. 11A). However, in the twisted strand design, the polymer covers the whole strand (FIG. 11B). When the polymer layer was evaluated under high magnification, it was found that the polymer is highly porous. This porosity greatly contributes to frictional forces since $$F_r = \mu N$$

where $F_r$ is the resistive force of friction, $\mu$ is the coefficient of friction for the two surfaces which relates to the surface roughness, and N is the normal force pushing the two objects together. Therefore, the friction between the hydrogel and twisted strand should be higher than the BOS design due to more coverage of the highly porous polymer layer.

Another factor that contributes to the difference in frictional forces is the geometry of the two designs. 3-D models were built based on the two designs. The twisted strand design model was simplified into 2 twisted strands rather than 4. Then, the section along the strand axis was checked. As shown in FIGS. 12A-B, for the BOS design, the beads provided smooth nodular interruptions along the straight strand edges. This nodular structure could increase the resistance along the strand surface to a certain point and could further increase the friction between the hydrogel and the reinforcement strand. Comparatively, in the twisted strand design, as can be seen in FIGS. 12C-D, the section image shows many "barbed" structures along the axis. Due to these "barbed" structures, the mechanical interaction between the hydrogel and reinforcement strand is not merely based on friction, but is also based on a unique structural interaction. It is believed that these structural blockages further contribute to the mechanical robustness of the entire device.

Example 3—Theoretical Wettability Analysis of the of the Single Strand and Twisted Strand Liquids tend to minimize their surface area by virtue of surface tension, which may cause liquid instability such as fluid break-up. A sphere is the geometric shape that has the smallest ratio of surface area to volume, so small quantities of liquids tend to form sphere-like droplets. In the case of a solid strand within a uniform liquid film, the capillary pressure will force the liquid out of the film and introduce a liquid instability. This instability causes the liquid film to undulate and to eventually break up into a string of droplets.

It has been reported that liquid films can stably exist on fibers when the wavelength $$(\lambda = 2\sqrt{2}\pi R)$$

is less than the circumference of the liquid cylinder coating the fiber $$(l = 2\pi(R+t))$$

(Quere, "Fluid Coating on a Fiber," *Annu. Rev. Fluid Mech.* 31:347-384 (1999), which is hereby incorporated by reference in its entirety). Here, t is the film thickness and R is the fiber radius. Thus, the upper limit of the film thickness is $t_{max}$, viz.

$$t_{max} = (\sqrt{2} - 1)R$$

Figure 13:
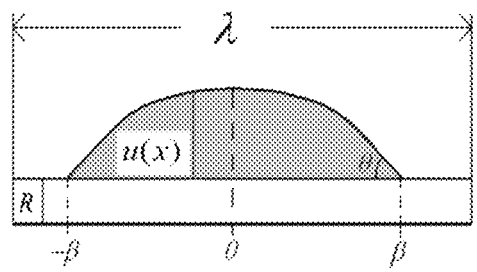
FIG. 13 is a diagram of a liquid droplet on a strand (barrel shape).

The original thickness of the liquid film $t_o$ is important to the liquid instability or the fluid break-up. Based on mass conservation, the value of $t_o$ can be inversely determined by the final volume and shape of the droplet when liquid loss due to evaporation is neglected. In FIG. 13, the volume of the droplet $V_f$ within one wavelength is given by $$V_f = \pi \int_{-\beta}^{\beta} [u(x) + R]^2 dx - 2\pi R^2 \beta$$

where β is the half-length of the droplet and u(x) is the droplet thickness in x-direction.

The original film thickness $t_o$ is readily obtained by solving the following equation $$\pi\lambda[(t_o+R)^2 - R^2] = V_f$$

It is evident that the original film is very thin and $t_o < t_{max}$ accounts for the instability of liquid films.

Figure 14:
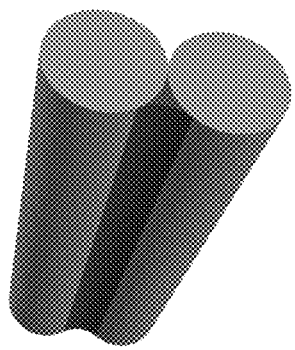
FIG. 14 is a perspective view showing a liquid film inside a wedge between two strands.

The parallel or twisted strands reduce liquid instability and fluid break-up due to the wedges between strands (see FIG. 14). In comparison to parallel strands, twisted strands have higher mechanical strength due to better contact and interaction between strands. Additionally, the deep wedges ensure the existence of continuous liquid films along the twisted strands.

It has been shown that the liquid attached to a solid edge with dihedral angle 2α is stable when $$\alpha + \theta < \pi/2$$

Figure 15:
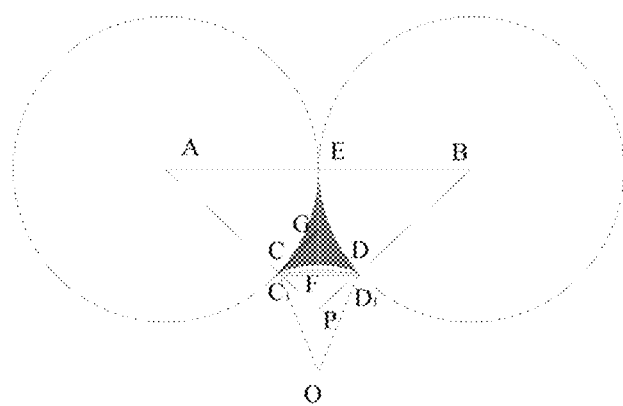
FIG. 15 is a cross-sectional view of a liquid within the wedge between two circular fibers (e.g., of the structure shown in FIG. 14).

(Langbein, "The Shape and Stability of Liquid Menisci at Solid Edges," *J. Fluid Mech.* 213:251-265 (1990), which is hereby incorporated by reference in its entirety). Here, θ is the contact angle and α is equivalent to ∠FGC (see FIG. 15). Considering the convex surface of circular strands, the arc length of $\overline{CE}$ is greater than the line length of $\overline{CG}$. Therefore, the deeper wedge between parallel or twisted strands leads to more stable liquid film, when $$\angle FGC + \angle OC_1P < \pi/2$$

or the liquid-vapor interface $\overline{CD}$ is concave (which is approximately observed in PPTs).

Next, the effect of gravity on the liquid stability was considered. If the gravity of the liquid column is much smaller than the capillary force, the liquid stability will be solely dependent on capillary effect and the gravity will be negligible. Based on the Gibbs free energy minimization method, the capillary pressure at the interface CD is given by $$\Delta p = \frac{\cos\theta\gamma}{R(1-\cos\alpha)\sin\alpha}$$

and the maximum pressure due to the gravity of liquid films is calculated as $$p_g = \frac{S\rho}{2R(1-\cos\alpha)}$$

It is expected that $$p_g << \Delta p.$$

The equations used in the models are as follows.

$$\frac{dU}{dh} = 0$$

$$dU = \gamma_{SL}dS_{SL} + \gamma_{SV}dS_{SV} + \gamma_{LV}dS_{LV} + \Delta p S dh$$

$$dS_{SL} = -dS_{SV} = L\overline{CC_1}$$

$$dS_{LV} = L(\overline{C_1D_1} - \overline{CD}) = 0$$

$$\gamma_{LV} = \gamma$$

$$\cos\theta = \frac{\gamma_{SV} - \gamma_{SL}}{\gamma}$$

$$\overline{CC_1} = \overline{CC_1}$$

$$\angle CAE = \alpha$$

$$\angle GCD = \angle CAE$$

$$\overline{CC_1} = \frac{dh}{\sin\alpha}$$

$$S = \overline{LCD} = \overline{LC_1D_1}$$

$$\overline{CD} = \overline{C_1D_1} = 2R(1-\cos\alpha)$$

$$dU = -2\cos\theta\gamma L\overline{CC_1} + \Delta p L \overline{C_1D_1} dh = -2\cos\theta\gamma L\frac{dh}{\sin\alpha} + \Delta p L 2R(1-\cos\alpha)dh$$

$$\frac{dU}{dh} = 0$$

$$\Delta p = \frac{\cos\theta\gamma}{R(1-\cos\alpha)\sin\alpha}$$

$$\frac{dU}{dh} = 0$$

$$S_{ACE} = S_{BDE} = \frac{\alpha}{2}R^2$$

$$\angle OC_1P = \theta$$

$$\angle C_1OP = \frac{\pi}{2} - \alpha - \theta$$

$$\overline{OC_1} = \frac{\overline{CD}}{2\sin\angle C_1OP} = \frac{R(1-\cos\alpha)}{\cos(\alpha+\theta)}$$

$$S_{COF} = \frac{1}{2}\left[\frac{R(1-\cos\alpha)}{\cos(\alpha+\theta)}\right]^2 \cos(\alpha+\theta)\sin(\alpha+\theta)$$

-continued $$S_{ABCD} = R^2(2 - \cos\alpha)\sin\alpha = R^2(2 - \cos\alpha)\sin\alpha +$$

$$\left[\frac{R(1-\cos\alpha)}{\cos(\alpha+\theta)}\right]^2 \cos(\alpha+\theta)\sin(\alpha+\theta) - \frac{1}{2}(\pi - 2\alpha - 2\theta)\left[\frac{R(1-\cos\alpha)}{\cos(\alpha+\theta)}\right]^2$$

$$p_g = \frac{S\rho}{2R(1-\cos\alpha)}$$

Example 4—Compartmentalized Nanofiber/Hydrogel Hybrid Microdevices for Cell Encapsulation, Culture, and Delivery Materials and Methods Chemicals and Characterizations. Polycaprolactam (nylon 6) was purchased from Scientific Polymer Products, Inc. (Ontario, NY). Formic acid, $CaCl_2$, and $BaCl_2$ were purchased from Sigma-Aldrich Co. (St. Louis, MO). Sodium alginate was purchased from FMC BioPolymer Co. (Philadelphia, PA). All reagents were purchased and used as received without further purification. The samples were characterized by different analytical techniques. Scanning electron microscopy (SEM) was performed by using a field emission scanning electron micro-analyzer (LEO 1550). Optical and fluorescent microscopic images were observed by a digital inverted microscope (EVOS fl). Conventional macro-tensile measurements were performed using a dynamic mechanical thermal analysis (DMA Q800). All samples were mounted between holders at a distance of ~1.5 cm. Tensile testing was conducted at a rate of 0.5 N/min at room temperature (23° C.). Stress (MPa) and strain (%) were automatically calculated by the software.

Fabrication of the Nanofiber-Reinforced Hydrogel Microdevices. In a typical synthetic procedure, a precursor solution of 20% (w/v) Nylon 6 and 5% (w/v) $CaCl_2$ in a mixture of formic acid was prepared. Then, a typical electrospinning process was carried out. $Ca^{2+}$ releasing Nylon 6 nanofibers were electrospun onto a rotating collector. Afterwards, the as-prepared nanofiber device was submerged in 2% alginate solution and put in vacuum chamber degasing for 15 min to make sure the alginate solution fully penetrated into the nanofiber devices. The device was put in $BaCl_2$/Mannitol/HEPES solution to enhance the crosslinking of the alginate hydrogel.

Islet Encapsulation and Transplantation. Islets were isolated from Sprague-Dawley rats by following a previously reported protocol. Islet equivalence was used to determine the number of the islets. For encapsulation, typically, 500 islets equivalences were collected and dispersed in 20 μL MATRIGEL™. The islets suspended in MATRIGEL™ solution were injected into the nanofiber-reinforced, hydrogel microdevice ("NHM") device by using a precooled syringe. After sealing the opening end, the device was washed with HEPES buffer and put in RPMI medium, ready for transplantation. To transplant the NHM device into mice, the mice were anesthetized and a 1 mm incision was made along the midline of the abdomen. An NHM device with predetermined number of islet equivalences was transplanted into the peritoneal cavity through the incision. The incision was closed by sutures and a wound clip.

Results and Discussion

A compartmentalized NHM for cell encapsulation, culture, and delivery was designed and built. This design takes advantages of two interacting materials: $Ca^{2+}$-releasing electrospun polymer nanofibers and $Ca^{2+}$-crosslinkable alginate hydrogel. Electrospun nanofiber membranes are a versatile class of material that has various attractive properties for use as biomaterials such as the small fiber size (~10 nm-10 μm), high porosity (>90%) and surface area (~10 m²/g), interconnected pore structures (~1 μm), and more importantly tunable material properties including mechanical strength, biodegradability and wettability. On the other hand, the alginate hydrogel can be easily crosslinked by divalent cations under physiological conditions; its biocompatibility has been well documented. In the NHM design, these two types of materials were combined to engineer $Ca^{2+}$-releasing nanofiber micropackages/microcontainers that crosslinked alginate in situ to form robust hybrid cell encapsulation microdevices.

The rationale of the NHM design is the following. First, the nanofiber membranes as the scaffolds of the microdevice walls provide the necessary mechanical strength and prevent any potential breakage or cell leakage while still allowing adequate mass transfer. Second, the alginate hydrogel as the microdevice exterior reinforced by the nanofibers through mechanical interlocking provide the necessary biocompatibility and immunoprotection. Third, the NHM can be pre-made and the cells can be loaded in a custom designed fashion, for example, by dispersing the cells in their preferred extracellular matrix proteins. This way, the NHM exterior hydrogel that interacts with the body and the hydrogel in the internal compartment that interacts with the cells can be decoupled and independently designed. Finally, multiple compartments can be engineered into a single NHM, which can then be used for complex cell encapsulation, co-culture, and delivery.

As described in this example, the NHM was fabricated with different compartmentalizations and the robust mechanical property was confirmed. Using both model cells and insulin-producing pancreatic islets, the facile mass transfer and flexible cell loading in single or multiple compartments with a control over the cell-dispersing matrix was demonstrated. Lastly, the biocompatibility, functionality, and retrievability of the NHM was evaluated by encapsulating and delivering rat islets into a chemically-induced diabetic mouse model. The diabetes was corrected for the duration of the experiment (8 weeks) right before the implants were retrieved. The retrieved devices showed minimal fibrosis according to histology studies and, as expected, live and functional islets were observed within the devices, confirming the great potential of the NHM as a new platform for cell encapsulation therapy.

To fabricate the NHM, nanofibers were first electrospun directly onto an aluminum rotating rod, as shown in FIG. 16A, to form nanofibrous microtubes. Different polymers (FIGS. 20A-J) could be spun, and Nylon was chosen due to its excellent mechanical property and wide usage as a clinically approved suture material. Unlike conventional electrospun fibers, the Nylon fibers developed here could release $Ca^{2+}$ ions pre-incorporated into the fibers by dissolving $CaCl_2$ in the Nylon precursor solution. The released $Ca^{2+}$ then automatically crosslinked the alginate molecules to form a thin layer of uniform hydrogel around the microtube in situ (FIG. 16B). The interconnected porous structures of the nanofibrous membrane allowed infusion of the alginate hydrogel and greatly enhanced its mechanical strength. To visualize this hybrid structure more clearly, a Rhodamine (red) fluorescent dye was incorporated into the Nylon nanofibers and the alginate was covalently labeled with an Alexa Fluor (green) dye, as shown in FIGS. 16C-E. More interestingly, NHMs with more complex, multicompartmental structures (FIG. 16F) can be fabricated by wrapping several microtubes together through an additional nanofiber deposition. The NHMs with multiple microcompartments will have many applications for co-encapsulation, culture, and delivery of different types of cells.

As shown in FIG. 17A, nanofibrous nylon microtubes of different sizes ranging from 300 μm to 3 mm (inner diameter) and nanofibrous devices with 2 to 4 microcompartments were fabricated. FIG. 17B shows scanning electron microscopy (SEM) images of the microtube and nanofiber membrane. The average diameter of individual Nylon fibers was around 200 nm. Although the exact pore structures of this nanofiber nonwoven were difficult to quantify, they were sufficiently tight so that the cells could not escape, while oxygen, nutrients, metabolic wastes, and therapeutic products were able to diffuse in and out freely. To confirm that the alginate hydrogel indeed penetrated the nanofiber membrane and that they were mechanically interlocked by the nanofiber structure, the NHM was freeze-dried first and then observed under SEM. As shown in FIG. 17C, the dehydrated alginate attached to the fibers and was uniformly distributed within the interstitial space. The inset digital photo and confocal image further revealed the watery appearance of the NHM at hydrated state and the thin (green) alginate hydrogel exterior, respectively. This tightly impregnated structure brings together the advantages of both the nanofibers and the hydrogel to the NHM. On one hand, the nanofibers are coated with more biocompatible alginate hydrogel; on the other hand, the soft hydrogel is reinforced by the tough nylon nanofibers, making it easier to handle and less likely to break or leak.

Next, the mechanical enhancement was quantified by comparing the elastic moduli among the nanofiber membrane, nanofiber-reinforced alginate hydrogel sheet and the sheet made of alginate hydrogel alone. The stress-strain curves in FIG. 17D clearly show that the mechanical properties of alginate hydrogel were greatly improved by Nylon nanofiber reinforcement. This is expected from the general rule of mixtures:

$$E_{total} = a_1 E_1 + a_2 E_2,$$

where $E_{total}$, $E_1$, $E_2$ are the Young's modulus of the composite material and the two different components, respectively; and $a_1$, $a_2$ are their respective cross-sectional area fractions.

The application of NHM for cell encapsulation and culture was demonstrated first by using a model cell line, MDA-MB-231 cells. The cells were dispersed in Matrigel™, a commercially available extracellular matrix favored by many cell types, and then injected into the NHM. After sealing at the open end with a drop of electrospinning solution, the NHM was put into culture and the cells were characterized. FIGS. 18A-B show cell viabilities right after encapsulation (FIG. 18A) and after 5 days of culture (FIG. 18B). The growth curves were obtained using MTT assays (FIG. 18C) where the control group was the same amount of MDA-MB-231 cells seeded onto petri dishes. Both the cell viability and the growth curve confirmed that the NHM was non-toxic and had sufficient mass transfer to support cell survival and proliferation.

Another cell line, GATA6WT, was utilized as an additional example of cell encapsulation where the cells were encapsulated in both tubular NHM and planer NHM devices. Similarly, high cell viability was observed. Next, the rat pancreatic islets were encapsulated using the NHM. Both the viability staining (FIG. 18D) and the immunostaining of the insulin (FIG. 18E) of the encapsulated islets after overnight culture confirmed once again that NHM supported the growth of the cells and cell aggregates. More importantly, the glucose-stimulated insulin secretion (GSIS) assay (FIG. 18F) indicated approximately the same level of insulin secretion upon glucose stimulation between the encapsulated islets and the control (islets cultured in medium), pointing to the facile mass transfer of not only nutrients but also the secreted insulin.

One unique feature in the NHM design is the compartmentalization (FIG. 16F), which enables encapsulation of different types of cells in individualized compartments, rather than a simple, random mixture. The cells are physically separated but soluble factors (chemokines and cytokines) are essentially interchangeable due to the high permeability of the membranes and the proximity of the cells located in different compartments. Such a system can have many applications as a novel, implantable platform for studying cell co-cultures, cell migrations, and paracrine signaling under both in vitro and in vivo environments. To provide a proof of concept, MDA-MB-231-EGFP (green) cells and MDA-MB-231-dTomato (red) cells were used as model cells for co-encapsulation. The two types of cells were seeded into two compartments within one single NHM as shown by the 2D (FIGS. 18G, 18H) and 3D (FIG. 18I) fluorescent images. In principle, more types of cells can be readily encapsulated, co-cultured and even delivered, all in a single microdevice.

Encouraged by the robust mechanical and mass transfer properties of the NHM and the anticipated biocompatibility and retrievability, an in vivo study was performed using a rat-to-mouse xenotransplantation model. Pancreatic islets isolated from Sprague-Dawley rats were encapsulated in NHM and transplanted into immunocompetent, streptozocin (STZ)-induced diabetic mice. C57BL/6 mice were chose as the donor because they were a challenging strain known to develop more fibrosis against alginate than other models, such as Balbc mice or Lewis rats. For each mouse, a 1 inch NHM device with 500 islet equivalences were implanted intraperitoneally. FIG. 19A shows the blood glucose concentrations (BG) over time post-transplantation. The diabetes was reversed 2 days after the implantation and remained cured (i.e., BG<200 mg/dL) for at least 8 weeks when the experiment was ended. The devices were then retrieved and all the mice went back to diabetic state, confirming the effectiveness of the NHM in regulating the blood glucose level and controlling the diabetes. FIG. 19B shows a typical photo of the retrieved devices; there was no visible tissue adhesion or extensive fibrosis on the devices. Histological studies (FIGS. 19C-D) revealed only a very thin (about one layer of cells) layer of cellular overgrowth, and more interestingly, the alginate hydrogel still firmly attached to the nanofiber membranes, consistent with the mechanical characterization (FIG. 17D). The islets observed from the retrieved devices (FIG. 19C) appeared to have distorted morphology, suggesting those islets might have experienced certain stress in this non-native environment. However, importantly, the islets seemed to be still functional after 8 weeks of implantation, as indicated by the positive insulin staining (FIG. 19E). Taken together, the data obtained from this in vivo experiment strongly suggested that the NHM was mechanically robust, biocompatible, easy to implant and retrieve, and had sufficient mass transfer for potential long-term clinical use.

In conclusion, this study shows a new type of cell encapsulation microdevice that can overcome some of the most daunting challenges in the field. The mechanical strength and unique micro/nano structures of electrospun fibers were taken advantage of to develop compartmentalized, $Ca^{2+}$-releasing nanofibrous micropackages. These micropackages were subsequently hybridized in situ with a more biocompatible alginate hydrogel that is infeasible to form mechanically stable microdevices on its own. Encapsulation and culture of several different types of cells including both single cells and cell aggregates was demonstrated. The multicompartmental microdevices are particularly interesting as they can provide a novel, implantable platform for cell co-culture, migration, and paracrine signaling assays that have typically been studied at present in in vitro multi-well formats (such as the multi-well TRANSWELL® systems). The therapeutic potential of the NHM was also demonstrated through a type 1 diabetic model using primary islets. More importantly, this encapsulation design is applicable to other types of cells, particularly those stem cell-derived ones where durability, sturdiness, and retrievability of the device are absolutely desirable due to the concern of potential teratoma formation. The fact that the cells can be loaded in a custom designed way with controlled extracellular matrix and space makes the NHM extremely useful to deliver cells that have certain proliferation potential. Finally, the NHM design is not limited to any polymer or hydrogel. In fact, the nanofibers can be made from a slowly biodegradable polymer that may release anti-inflammatory drugs to mitigate the fibrosis, while the hydrogel can be made from an ultra-compatible, chemically modified alginate, a photo-crosslinkable polyethylene glycol (FIGS. 21A-D), or a foreign body response-resistant zwitterionic polymer. In the latter cases, the nanofibrous structures will again play an important role, not only to hold the precursor solution in place through capillary action to facilitate the crosslinking, but also enhance the mechanical properties of the final devices.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An implantable therapeutic delivery system comprising:
   a nanofibrous core substrate comprising one or more internal spaces wherein one or more therapeutic agents is positioned in the one or more internal spaces; and
   an outer biocompatible polymeric coating surrounding said nanofibrous core substrate,
   wherein the nanofibrous core substrate contains divalent cations.

2. The implantable therapeutic delivery system according to claim 1, wherein the nanofibrous core substrate and the outer biocompatible polymeric coating are crosslinked to each other.

3. The implantable therapeutic delivery system according to claim 1, wherein the one or more therapeutic agents is insulin.

4. The implantable therapeutic delivery system according to claim 1, wherein the one or more therapeutic agents is released from a preparation of cells positioned in the one or more internal spaces of the nanofibrous core substrate.

5. The implantable therapeutic delivery system according to claim 4, wherein the preparation of cells is a preparation of islet cells that release insulin.

6. The implantable therapeutic delivery system according to claim 4, wherein the preparation of cells is a preparation of stem cells or stem cell derived cells.

7. The implantable therapeutic delivery system according to claim 4, wherein the one or more therapeutic agents is fibrinogen or Factor VIII.

8. The implantable therapeutic delivery system according to claim 1 further comprising:
   one or more therapeutic agents positioned in the outer biocompatible polymeric coating surrounding said nanofibrous core substrate.

9. The implantable therapeutic delivery system according to claim 1, wherein the one or more internal spaces comprises two or more discrete compartments.

10. The implantable therapeutic delivery system according to claim 1, wherein the nanofibrous core substrate is formed by electro-spinning fibers of core material into a porous, shaped article defining the one or more internal spaces.

11. The implantable therapeutic delivery system according to claim 1, wherein the outer biocompatible polymeric coating is a hydrogel material.

12. The implantable therapeutic delivery system according to claim 11, wherein the hydrogel material comprises alginate.

13. The implantable therapeutic delivery system according to claim 1, wherein the nanofibrous core substrate comprises a material selected from the group consisting of nylon, silk, poly(ether sulfone), polypropylene, polyester, polybutester, gelatin, chitosan, hyaluronic acid, silk fibroin, collagen, poly(lactic acid), polyurethane, polycarbonate, polyethylene, polydimethylsiloxane, polymethylmethacrylate, poly(ε-caprolactone), poly(lactic-co-glycolic acid), poly(ethylene-co-vinylacetate), and poly(l-lactide-co-ε-caprolactone).

* * * * *